(12) United States Patent
Chebotareva et al.

(10) Patent No.: US 8,685,541 B2
(45) Date of Patent: Apr. 1, 2014

(54) DIBENZOFURANE POLYMERS FOR ELECTROLUMINISCENT DEVICES

(75) Inventors: Natalia Chebotareva, Hagenthal le Bas (FR); Roger Pretot, Basel (CH); Paul Adriaan Van Der Schaaf, Hagenthal-le-Haut (FR); Annemarie Wolleb, Fehren (CH); Heinz Wolleb, Fehren (CH)

(73) Assignee: BASF SE, Ludwigshafen (DE)

( * ) Notice: Subject to any disclaimer, the term of this patent is extended or adjusted under 35 U.S.C. 154(b) by 489 days.

(21) Appl. No.: 12/994,887

(22) PCT Filed: May 19, 2009

(86) PCT No.: PCT/EP2009/056037
§ 371 (c)(1),
(2), (4) Date: Nov. 29, 2010

(87) PCT Pub. No.: WO2009/147011
PCT Pub. Date: Dec. 10, 2009

(65) Prior Publication Data
US 2011/0086454 A1    Apr. 14, 2011

(30) Foreign Application Priority Data
Jun. 2, 2008    (EP) .................... 08157389

(51) Int. Cl.
*H01L 51/54*    (2006.01)

(52) U.S. Cl.
USPC ........... 428/690; 428/917; 313/504; 313/505; 313/506; 257/40; 257/E51.05; 257/E51.026; 257/E51.032; 548/304.4; 548/418; 548/440

(58) Field of Classification Search
USPC ................. 428/690, 917; 313/504, 505, 506; 257/40, E51.05, E51.026, E51.032; 548/448, 304.4, 418, 440
See application file for complete search history.

(56) References Cited

U.S. PATENT DOCUMENTS

| 2,527,223 | A | 10/1950 | Kern |
| 3,294,763 | A | 12/1966 | Hewett |
| 2002/0027623 | A1 | 3/2002 | Doi et al. |
| 2003/0082405 | A1 * | 5/2003 | Taguchi .................... 428/690 |
| 2007/0248840 | A1 | 10/2007 | Lin et al. |
| 2010/0045171 | A1 | 2/2010 | Katakura |

FOREIGN PATENT DOCUMENTS

| EP | 1 138 746 | A | 10/2001 |
| FR | 1441442 | A | 6/1966 |
| GB | 601568 | | 5/1948 |
| GB | 1077086 | A | 7/1967 |
| WO | 2008/029652 | A | 3/2008 |
| WO | 2008/029729 | A1 | 3/2008 |
| WO | 2009/092671 | A2 | 7/2009 |

OTHER PUBLICATIONS

Hewett et al., The synthesis and polymerization of 4-vinyldibenzofuranand 4-vinyldibenzothiophene, 1968, Polymer Letters, vol. 6, pp. 565-571.*
Gilman et, al., Dibenzofurans. XI. Substituents in the 1-Position, 1939, Journal of American Chemical Society, Vo. 61, pp. 1365-1371.*

* cited by examiner

*Primary Examiner* — Gregory Clark
(74) *Attorney, Agent, or Firm* — Shiela A. Loggins

(57) ABSTRACT

Disclosed are electroluminescent materials comprising a homopolymer based on recurring structural units of the formula (I) wherein $R^9$, $R^{9'}$ $R^{9''}$, $R^{11}$, $R^{13}$ $R^{14}$, $R^{11'}$, $R^{13'}$, $R^{14'}$ independently are H or an organic substituent, where at least one of $R^9$, $R^{9'}$ $R^{9''}$, $R^{11}$, $R^{13}$ $R^{14}$, $R^{11'}$, $R^{13'}$, $R^{14'}$ comprises a group $R^{10}$ of the formula $-(Sp)_{x10}$-[PG']< wherein Sp is a divalent organic spacer, PG' is a group derived from a polymerizable group, and x10 is 0 or 1, with substituents and spacer as defined in claim 1. Further disclosed are some novel polymers of this class as well as monomers for their preparation. The homopolymers are advantageously used as a host material in devices further comprising a luminescent component, which is usually selected from phosphorescent metal complexes and fluorescent dopants.

9 Claims, No Drawings

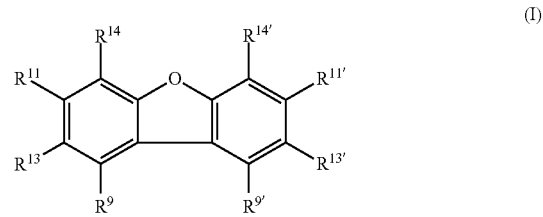

(I)

DIBENZOFURANE POLYMERS FOR ELECTROLUMINISCENT DEVICES

The present invention pertains to some novel electroluminiscent materials, some novel materials (especially polymers) for their preparation, a process for the preparation of the novel electroluminiscent materials, as well as electroluminiscent devices containing the novel electroluminiscent materials or polymers, and corresponding uses.

Some dibenzofurane homopolymers have been mentioned in GB-601568, U.S. Pat. No. 3,294,763, FR-1441442 and GB-1077085, inter alia as photoconducting materials. WO 08/029652 discloses some oligomers and polymers inter alia combining carbazole and dibenzofurane units.

It has now been found that certain side chain dibenzofurane polymers may replace commonly used polyvinylcarbazole (PVK) as a host material in OLEDs, especially for Iridium based triplett emitters (TEs), and give high quantum yield and efficiency.

The invention therefore pertains to an electroluminescent material comprising a homopolymer based on recurring structural units of the formula I

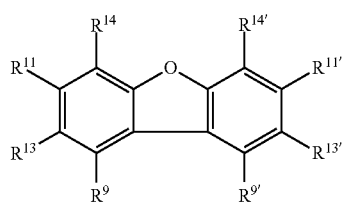

(I)

wherein
$R^9, R^{9'} R^{9''}, R^{11}, R^{13}, R^{14}, R^{11'}, R^{13'}, R^{14''}$ independently are H or an organic substituent, where at least one of $R^9, R^{9'} R^{9''}, R^{11}, R^{13}, R^{14}, R^{11'}, R^{13'}, R^{14''}$ comprises a group $R^{10}$ of the formula —(Sp)$_{x10}$-[PG']< wherein Sp is a divalent organic spacer, PG' is a group derived from a polymerisable group, and x10 is 0 or 1.

Any organic substituent in formula I, if present, is usually selected from halogen; OH; $C_1$-$C_{24}$alkoxy; $C_2$-$C_{24}$alkoxy which is substituted by E and/or interrupted by D; $C_1$-$C_{24}$alkyl; $C_1$-$C_{24}$alkyl which is substituted by E and/or interrupted by D; $C_1$-$C_{24}$haloalkyl; $C_2$-$C_{24}$alkenyl; $C_2$-$C_{24}$alkynyl; $C_1$-$C_{24}$alkylthio; $C_1$-$C_{24}$acyl; $C_5$-$C_{24}$aryl; $C_6$-$C_{24}$aryl which is substituted by G; $C_1$-$C_{20}$heteroaryl; $C_2$-$C_{20}$heteroaryl which is substituted by G; $C_7$-$C_{25}$aralkyl; $C_3$-$C_{12}$cycloalkyl; $C_1$-$C_{24}$acyloxy; $C_5$-$C_{10}$aryloxy; $C_3$-$C_{12}$cycloalkyloxy; COR; CH=NR; CH=N—OH; CH=N—OR; COOR; OCOR; CONHR; NHCOR; CONRR'; CONH—NHR; CONH—NRR'; SR; SO$_2$R; SO$_3$R; SO$_2$NHR; SO$_2$NRR'; SO$_2$NH—NHR; SO$_2$NH—NRR'; S(O)R; S(O)OR; S(O)NHR; S(O)NRR'; S(O)NH—NHR; S(O)NH—NRR'; SiRR'R''; GeRR'R''; PRR'; PORR'; PO(OR)R'; PO(OR)$_2$; PO(NHR)$_2$; PO(NRR')$_2$; CN; NO$_2$; NHR; NRR'; NH—NHR; NH—NRR', CONROH;

where R, R' and R'' independently are selected from $C_1$-$C_{12}$alkyl, $C_1$-$C_{12}$haloalkyl, $C_5$-$C_{10}$aryl, $C_3$-$C_{12}$cycloalkyl; and R may also be hydrogen;
or two substituents $R^9, R^{11}, R^{13}, R^{14}, R^{9'}, R^{11'}, R^{13'}$ and $R^{14'}$, which are adjacent to each other, together form a group

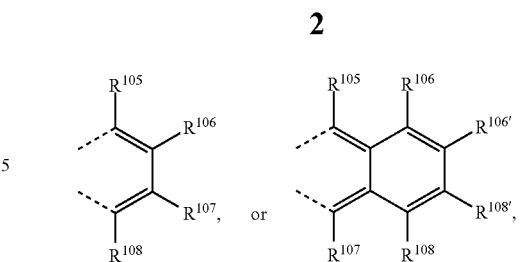

$R^{105}, R^{106}, R^{107}, R^{108}, R^{105'}, R^{106'}, R^{107'}$ and $R^{108'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D;

D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—;
and
E is —OR$^{29}$; —SR$^{29}$; —NR$^{25}$R$^{26}$; —COR$^{28}$; —COOR$^{27}$; —CONR$^{25}$R$^{26}$; —CN; or halogen;
G is E, $C_1$-$C_{18}$alkyl, $C_3$-$C_{12}$cycloalkyl, $C_2$-$C_{18}$alkyl which is interrupted by D, $C_1$-$C_{18}$perfluoroalkyl, or $C_1$-$C_{18}$alkoxy which is substituted by E and/or interrupted by D, wherein $R^{23}, R^{24}, R^{25}$ and $R^{26}$ are independently of each other H; $C_6$-$C_{18}$aryl; $C_6$-$C_{18}$arylalkyl; $C_3$-$C_{12}$cycloalkyl; $C_6$-$C_{18}$aryl or $C_6$-$C_{18}$arylalkyl which is substituted by $C_1$-$C_{18}$alkyl and/or $C_1$-$C_{18}$alkoxy; $C_1$-$C_{18}$alkyl; or $C_2$-$C_{18}$alkyl which is interrupted by —O—; or
$R^{25}$ and $R^{26}$ together form a five or six membered ring;
$R^{27}$ and $R^{28}$ are independently of each other H; $C_6$-$C_{18}$aryl; $C_6$-$C_{18}$arylalkyl; $C_6$-$C_{18}$aryl or $C_6$-$C_{18}$arylalkyl which is substituted by $C_1$-$C_{18}$alkyl and/or $C_1$-$C_{18}$alkoxy; $C_1$-$C_{18}$alkyl; $C_3$-$C_{12}$cycloalkyl; or $C_2$-$C_{18}$alkyl which is interrupted by —O—;
$R^{29}$ is H; $C_6$-$C_{18}$aryl; $C_6$-$C_{18}$arylalkyl; $C_6$-$C_{18}$aryl or $C_6$-$C_{18}$arylalkyl which is substituted by $C_1$-$C_{18}$alkyl and/or $C_1$-$C_{18}$alkoxy; $C_1$-$C_{18}$alkyl; $C_2$-$C_{18}$alkylcarbonyl; $C_3$-$C_{12}$cycloalkyl; or $C_2$-$C_{18}$alkyl or $C_2$-$C_{18}$alkylcarbonyl which is interrupted by —O—;
$R^{30}$ and $R^{31}$ are independently of each other $C_1$-$C_{18}$alkyl, $C_3$-$C_{12}$cycloalkyl, $C_6$-$C_{18}$aryl, or $C_6$-$C_{18}$aryl, which is substituted by $C_1$-$C_{18}$alkyl, and
$R^{32}$ is $C_1$-$C_{18}$alkyl, $C_6$-$C_{18}$aryl, or $C_6$-$C_{18}$aryl, which is substituted by $C_1$-$C_{18}$alkyl, R, R' and R'' independently are selected from $C_1$-$C_{12}$alkyl, $C_1$-$C_{12}$haloalkyl, $C_5$-$C_{10}$aryl, $C_5$-$C_{10}$aryl, $C_3$-$C_{12}$cycloalkyl, preferably from $C_1$-$C_6$alkyl, phenyl, cyclopentyl, cyclohexyl; and
Ar independently is selected from $C_5$-$C_{10}$aryl, or $C_5$-$C_{10}$aryl which is substituted by $C_1$-$C_{18}$ alkyl;
and one of $R^9, R^{9'} R^{9''}, R^{11}, R^{13}, R^{14}, R^{11'}, R^{13'}, R^{14'}, R^{105}, R^{106}, R^{107}, R^{108}, R^{105'}, R^{106'}, R^{107'}, R^{108'}$ is a group $R^{10}$ of the formula —(Sp)$_{x10}$-[PG']< wherein Sp is a divalent organic spacer, PG' is a group derived from a polymerisable group, and x10 is 0 or 1.

The spacer unit Sp, which may be present in the group $R^{10}$, typically is of the formula (X$_3$-D)$_{x11}$-X$_2$, wherein x11 is 0 or 1; X$_3$, X$_2$ independently are O, $C_1$-$C_4$alkylene-O, CH$_2$—CHOH—CH$_2$—O, S, $C_1$-$C_4$alkylene-S, NR22, $C_1$-$C_4$alkylene-NR22, COO, $C_1$-$C_4$alkylene-COO or $C_1$-$C_4$alkylene-OCO, CONR22, $C_1$-$C_4$alkylene-CONR22 or $C_1$-$C_4$alkylene-NR22CO, NR22CONR22, $C_1$-$C_4$alkylene-NR22CONR22, $C_1$-$C_4$alkylene, CH$_2$CHOHCH$_2$, or a direct bond, and D is $C_1$-$C_{24}$alkylene, interrupted $C_3$-$C_{24}$alkylene, $C_2$-$C_{24}$alkenylene, $C_2$-$C_{24}$alkynylene, $C_6$-$C_{10}$arylene. Preferred spacer units Sp are $X_2$ (i.e. those of the above wherein x11 is 0), where $X_2$ is a direct bond, O, $C_1$-$C_4$alkylene-O, $CH_2$—CHOH—$CH_2$—O, COO, CONR22, $C_1$-$C_4$alkylene, or $CH_2CHOHCH_2$.

PG' is a group derived from a polymerisable group, it is trivalent since it is anchored on Sp (or its anchor position in formula I) and it is integrated in the polymer chain, or crosslinked polymer network, of the present invention. A typical group of moieties PG' thus are derived from ethylenically unsaturated monomers or strained oxygen ring systems, including those of the formulae

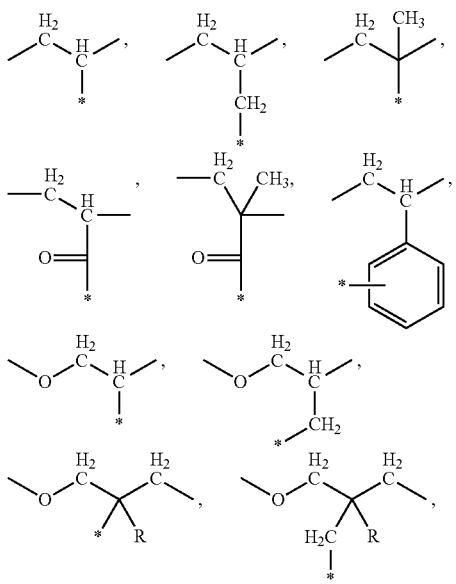

where the asterisk (*) indicates its bonding position to Sp or the moieties of formula I and R is as defined above, while the 2 further open bonds provide integration into the polymer chain. These moieties are especially suitable for introducing the desired functionalities as side chains into the final polymer of the invention, or as crosslinking moieties. Corresponding polymerizable groups PG include vinyl, allyl, 1-methylvinyl (isopropenyl), (meth)acryloyl, vinylphenyl (styryl), oxiranyl, glycidyl, oxetanyl etc. Other moieries PG' are those derived from from moieties PG described further above, e.g. those introducing the desired functionalities into the main chain of the polymer of the invention.

The homopolymers used in the electroluminescent materials of the invention may be isotactic or syndiotactic or, usually, atactic.

The electroluminescent material further comprises a luminiscent component usually selected from phosphorescent metal complexes and fluorescent dopants as known in the art.

The present polymers show especially good results with regard to solution processing or printing (e.g. in case of non-crosslinked polymers), long-term stability of the electroluminescent device (e.g. resistance against migration/segregation/crystallization as well as against oxidation/heat) as well as its brightness and efficiency.

The term "ligand" is intended to mean a molecule, ion, or atom that is attached to the coordination sphere of a metallic ion. A "monodentate ligand" contains only 1 coordination site, while a "bidentate ligand" contains 2 coordination sites, both of which are attached to the metallic centre. The term "complex", when used as a noun, is intended to mean a compound having at least one metallic ion and at least one ligand. The term "group" or "moiety" is intended to mean a part of a compound, such as a substituent in an organic compound or a ligand in a complex. The term "substituted" is intended to mean replacement of a hydrogen atom in an organic group or compound by a (typically organic) substituent.

The term "organic substituent" stands for an organic (i.e. C, H containing) or (hetero)functional radical (e.g. consisting of heteroatoms and optionally either of C or H); usually, any organic substituent, if present, makes up a minor part of the compound; examples for organic substituents are organic radicals containing 1 to 20 carbon atoms and optionally further (e.g. 1-10) heteroatoms, heterofunctional radicals typically comprising 1 to 5 heteroatoms.

Heteroatoms in organic or heterofunctional radicals are usually selected from O, S, N, P, Si, B, as well as halogen (i.e. any of F, Cl, Br, I; in the electroluminescent material of the invention especially fluoro) making up such a radical.

Organic substituents, if present, often are selected from halogen, OH, $C_1$-$C_{24}$alkoxy, $C_1$-$C_{24}$alkyl, $C_1$-$C_{24}$haloalkyl, $C_2$-$C_{24}$alkenyl, $C_2$-$C_{24}$alkynyl, $C_1$-$C_{24}$alkylthio, $C_1$-$C_{24}$acyl, $C_5$-$C_{10}$aryl, $C_1$-$C_{10}$heteroaryl, $C_3$-$C_{12}$cycloalkyl, $C_1$-$C_{24}$acyloxy, $C_5$-$C_{10}$aryloxy, $C_3$-$C_{12}$cycloalkyloxy, or from the residues COR (i.e. aldehyde or keto group), CH=NR, CH=N—OH, CH=N—OR, COOR, OCOR, CONHR, NHCOR, CONRR', CONH—NHR, CONH—NRR', SR, $SO_2$R, $SO_3$R, $SO_2$NHR, $SO_2$NRR', $SO_2$NH—NHR, $SO_2$NH—NRR', S(O)R, S(O)OR, S(O)NHR, S(O)NRR', S(O)NH—NHR, S(O)NH—NRR', a silyl or germanyl group (SiRR'R", GeRR'R"), PORR', PO(OR)R', PO(OR)$_2$, PO(NHR)$_2$, PO(NRR')$_2$, cyano (CN), $NO_2$, NHR, NRR', NH—NHR, NH—NRR', CONROH;

where R, R' and R" independently are selected from $C_1$-$C_{12}$alkyl, $C_1$-$C_{12}$haloalkyl, $C_5$-$C_{10}$aryl, $C_3$-$C_{12}$cycloalkyl, preferably from $C_1$-$C_6$alkyl, phenyl, cyclopentyl, cyclohexyl;

and R may also be hydrogen. Common substituents are often selected from $C_1$-$C_{12}$alkyl, a hydroxyl group, a mercapto group, $C_1$-$C_{12}$alkoxy, $C_1$-$C_{12}$alkylthio, halogen, halo-$C_1$-$C_{12}$alkyl, a cyano group, an aldehyde group, a ketone group, a carboxyl group, an ester group, a carbamoyl group, an amino group, a nitro group or a silyl group.

Any condensed ring or ring system formed by two neighbouring residues such as $Q^1$ and $Q^2$ or two residues $R^{41}$ (see below) as an organic bridging group, together with their anchor atoms form a carbocyclic or heterocyclic, non-aromatic or preferably aromatic ring, typically of 5 to 7 ring atoms in total, often is selected from aryl, heteroaryl, cycloalkyl, or cycloaliphatic unsaturated moieties as explained below.

The term "haloalkyl" means groups given by partially or wholly substituting the above-mentioned alkyl group with halogen, the term includes $C_1$-$C_{24}$perfluoroalkyl, which is branched or unbranched, such as for example —$CF_3$ (trifluoromethyl), —$CF_2CF_3$, —$CF_2CF_2CF_3$, —$CF(CF_3)_2$, —$(CF_2)_3CF_3$, and —$C(CF_3)_3$.

The "aldehyde group, ketone group, ester group, carbamoyl group and amino group" include those substituted by an $C_1$-$C_{24}$alkyl group, a $C_4$-$C_{18}$cycloalkyl group, an $C_6$-$C_{30}$aryl group, an $C_7$-$C_{24}$aralkyl group or a heterocyclic group, wherein the alkyl group, the cycloalkyl group, the aryl group, the aralkyl group and the heterocyclic group may be unsubstituted or substituted. The term "silyl group" more specifically means a group of formula —$SiR^{105}R^{106}R^{107}$, wherein $R^{105}$, $R^{106}$ and $R^{107}$ are independently of each other a $C_1$-$C_8$alkyl group, in particular a $C_1$-$C_4$ alkyl group, a $C_6$-$C_{24}$aryl group or a $C_7$-$C_{12}$aralkylgroup, such as a trimethylsilyl group.

If a substituent occurs more than one time in a group, it can be different in each occurrence.

Alkyl stands for any acyclic saturated monovalent hydrocarbyl group; alkenyl denotes such a group but containing at least one carbon-carbon double bond (such as in allyl); similarly, alkynyl denotes such a group but containing at least one carbon-carbon triple bond (such as in propargyl). In case that an alkenyl or alkynyl group contains more than one double bond, these bonds usually are not cumulated, but may be arranged in an alternating order, such as in —[CH═CH—]$_n$ or —[CH═C(CH$_3$)—]$_n$, where n may be, for example, from the range 2-50. Where not defined otherwise, preferred alkyl contains 1-22 carbon atoms; preferred alkenyl and alkynyl each contains 2-22 carbon atoms, especially 3-22 carbon atoms.

The term alkyl, whereever used, thus mainly embraces especially uninterrupted and, where appropriate, substituted $C_1$-$C_{22}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—; alkylthio is alkyl-S—.

The term alkenyl, whereever used, thus mainly embraces especially uninterrupted and, where appropriate, substituted $C_2$-$C_{22}$alkenyl such as vinyl, allyl, etc.

Alkynyl, including $C_{2-24}$alkynyl, is straight-chain or branched, preferred is $C_{2-8}$alkynyl. For example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Where indicated as interrupted, any alkyl or alkylene moiety of more than one, especially more than 2 carbon atoms, or such alkyl or alkylene moieties which are part of another moiety, may be interrupted by a non-aromatic cyclic or aromatic cyclic (arylene or heteroarylene) moiety as defined below and/or preferably by a heterofunction such as O, S, CO, COO, OCNR22, OCOO, OCONR22, NR22CNR22, or NR22, where R22 is H, $C_1$-$C_{12}$alkyl, $C_3$-$C_{12}$cycloalkyl, phenyl. They can be interrupted by one or more of these spacer groups, one group in each case being inserted, in general, into one carbon-carbon bond, with hetero-hetero bonds, for example O—O, S—S, NH—NH, etc., not occurring; if the interrupted alkyl is additionally substituted, the substituents are generally not α to the heteroatom. If two or more interrupting groups of the type —O—, —NR22-, —S— occur in one radical, they often are identical.

Acyl stands for a residue of an organic carboxylic acid, from which it may be formally derived by abstraction of the acid OH; examples are formyl, acetyl, propionyl, benzoyl. Generally, $C_1$-$C_{18}$ acyl stands for a radical X'—$R_{21}$, wherein X' is CO or SO$_2$ and $R_{21}$ is selected from monovalent aliphatic or aromatic organic residues, usually from molecular weight up to 300; for example, $R_{21}$ may be selected from $C_1$-$C_{18}$alkyl, $C_2$-$C_{18}$alkenyl, $C_5$-$C_{19}$aryl which may be unsubstituted or substituted by $C_1$-$C_8$alkyl or halogen or $C_1$-$C_8$alkoxy, $C_6$-$C_{15}$arylalkyl which may be unsubstituted or substituted in the aromatic part by $C_1$-$C_8$alkyl or halogen or $C_1$-$C_8$alkoxy, $C_4$-$C_{12}$cycloalkyl, and in case that X' is CO, $R_{21}$ may also be H. Acyl is preferably an aliphatic or aromatic residue of an organic acid —CO—$R_{21}$, usually of 1 to 30 carbon atoms, wherein $R_{21}$ embraces aryl, alkyl, alkenyl, alkynyl, cycloalkyl, each of which may be substituted or unsubstituted and/or interrupted as described elsewhere inter alia for alkyl residues, or R' may be H (i.e. COR' being formyl). Preferences consequently are as described for aryl, alkyl etc.; more preferred acyl residues are substituted or unsubstituted benzoyl, substituted or unsubstituted $C_1$-$C_{17}$alkanoyl or alkenoyl such as acetyl or propionyl or butanoyl or pentanoyl or hexanoyl, substituted or unsubstituted $C_5$-$C_{12}$cycloalkylcarbonyl such as cyclohexylcarbonyl.

Aralkyl is, within the definitions given, usually selected from $C_7$-$C_{24}$aralkyl radicals, preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl. or 3-methyl-5-(1',1',3',3'-tetramethyl-butyl)-benzyl.

Non-aromatic cyclic (i.e. cycloaliphatic) moieties include cycloalkyl, aliphatic heterocyclic moieties, as well as unsaturated variants thereof such as cycloalkenyl. Cycloalkyl such as $C_3$-$C_{18}$cycloalkyl, is preferably $C_3$-$C_{12}$cycloalkyl or said cycloalkyl substituted by one to three $C_1$-$C_4$alkyl groups, and includes cyclopropyl, cyclobutyl, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred. $C_3$-$C_{12}$cycloalkyl includes cyclopropyl, cyclobutyl, cyclopentyl, cyclohexyl, cycloheptyl, cyclooctyl, cyclononyl, cyclodecyl, cycloundecyl, cyclododecyl; preferred among these residues are $C_3$-$C_6$cycloalkyl as well as cyclododecyl, especially cyclohexyl. Further ring structures occuring are heterocyclic aliphatic rings usually containing 5 to 7 ring members, among them at least 1, especially 1-3, heteromoieties, usually selected from O, S, NR22, where R22 is as explained above for interrupting NR22-groups; examples include $C_4$-$C_{18}$cycloalkyl, which is interrupted by S, O, or NR22, such as piperidyl, tetrahydrofuranyl, piperazinyl and morpholinyl. Unsaturated variants may be derived from these structures by abstraction of a hydrogen atom on 2 adjacent ring members with formation of a double bond between them.; an example for such a moiety is cyclohexenyl.

Wherever "aryl" is used (e.g. in $C_5$-$C_{10}$aryl, $C_1$-$C_{14}$-heteroaryl), it denotes an aromatic ring or polycyclic ring system containing the highest possible number of double bonds, such as preferably phenyl, naphthyl, anthrachinyl, anthracenyl, phenanthrenyl or fluorenyl. The term aryl mainly embraces hydrocarbon aromatic rings, examples mainly are $C_6$-$C_{18}$aryl including phenyl, naphthyl, anthrachinyl, anthracenyl, phenanthrenyl, fluorenyl. Heteroaromatic rings such as $C_1$-$C_{18}$heteroaryl moieties contain, as part of the ring structure, one or more heteroatoms mainly selected from O, N and S; heteroaryl such as $C_4$-$C_{18}$heteroaryl stands for an aryl group containing at least one heteroatom, especially selected from N, O, S, among the atoms forming the aromatic ring; examples include pyridyl, pyrimidyl, pyridazyl, pyrazyl, thienyl, benzothienyl, pyrryl, furyl, benzofuryl, indyl, carbazolyl, benzotriazolyl, thiazolyl, chinolyl, isochinolyl, triazinyl, tetrahydronaphthyl, thienyl, pyrazolyl, imidazolyl. Preferred are $C_6$-$C_{10}$aryl or $C_4$-$C_{18}$heteroaryl, e.g. selected from phenyl, naphthyl, pyridyl, tetrahydronaphthyl, furyl, thienyl, pyrryl, chinolyl, isochinolyl, anthrachinyl, anthracenyl, phenanthrenyl, pyrenyl, benzothiazolyl, benzoisothiazolyl, benzothienyl, especially $C_6$-$C_{10}$aryl; most preferred is phenyl, naphthyl. Any "arylene" stands for the corresponding divalent "aryl".

Examples are monomers containing one or more polymerizable groups (PG) such as ethylenically unsaturated moieties or strained ring systems. PG often is a polymerisable group selected from —C($R^{44}$)=$CH_2$, —NHC(O)—C($R^{45}$)=$CH_2$, —$OCH_2CH_2OC$(O)—C($R^{45}$)=$CH_2$, —OC(O)—C($R^{45}$)=$CH_2$, —C(O)—C($R^{46}$)=$CH_2$, —C≡C—, —C≡$CR^{46}$, —N≡C, —O—CH($CH_2CH_2CH$=$CH_2$)$_2$; $C_5$-$C_8$cycloalkenyl, bicycloalkenyl (a substituted or unsubstituted bicycloalkenyl group having 5 to 30 carbon atoms),

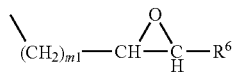

(1,2-epoxyether),

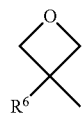

(oxetanyl),

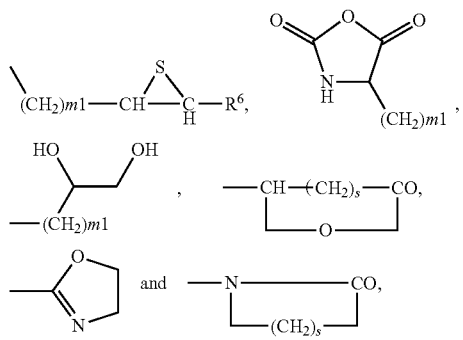

wherein s is an integer from 1 to 6, m1 is an integer from 1 to 6, $R^6$ is hydrogen, or $C_1$-$C_{20}$alkyl, $R^{44}$ is hydrogen, or $C_1$-$C_4$alkyl, or halogen, $R^{45}$ is hydrogen, $C_1$-$C_4$alkyl, or halogen, and $R^{46}$ is hydrogen, $C_1$-$C_4$alkyl, or $C_6$-$C_{12}$aryl, or PG' is a group derived from a polymerisable group

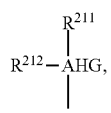

wherein
AHG is an aromatic, or heteroaromatic residue, which can optionally be substituted, such as

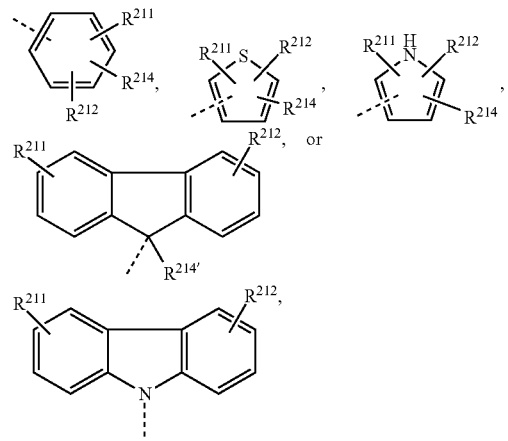

wherein each dotted line marks the bonding position of PG', $R^{211}$ and $R^{212}$ are independently of each other halogen, —C≡CH, boronic acid, or boronic esters, —Mg-Hal, —Zn-Hal, —Sn ($R^{213}$)$_3$, wherein Hal is halogen, and $R^{213}$ is $C_1$-$C_{18}$alkyl, $R^{214}$ and $R^{214'}$ are independently of each other H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or $C_7$-$C_{25}$aralkyl. Examples for preferred groups PG are vinyl, allyl, (meth)acryloyl, styryl, oxetanyl, oxiranyl, glycidyl.

If PG is a polymerisable group

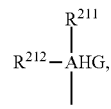

the following processes can be used for the production of polymers:

Polymerization processes involving only dihalo-functional reactants may be carried out using nickel coupling reactions. One such coupling reaction was described by Colon et al. in J. Pol. Sci., Part A, Polymer Chemistry Edition 28 (1990) 367, and by Colon et al. in J. Org. Chem. 51 (1986) 2627. The reaction is typically conducted in a polar aprotic solvent (e.g., dimethylacetamide) with a catalytic amount of nickel salt, a substantial amount of triphenylphosphine and a large excess of zinc dust. A variant of this process is described by Ioyda et al. in Bull. Chem. Soc. Jpn, 63 (1990) 80 wherein an organo-soluble iodide was used as an accelerator.

Another nickel-coupling reaction was disclosed by Yamamoto in Progress in Polymer Science 17 (1992) 1153 wherein a mixture of dihaloaromatic compounds was treated with an excess amount of nickel (1,5-cyclooctadiene) complex in an inert solvent. All nickel-coupling reactions when applied to reactant mixtures of two or more aromatic dihalides yield essentially random polymers. Such polymerization reactions may be terminated by the addition of small amounts of water to the polymerization reaction mixture, which will replace the terminal halogen groups with hydrogen groups. Alternatively, a monofunctional aryl halide may be used as a chain-terminator in such reactions, which will result in the formation of a terminal aryl group.

In general, polymerization methods and workup procedures known in the pertinent art may be applied in analogy for the present polymers, including those known as Heck, Sonogashira, Kumada reactions; reactions may be carried out e.g. in analogy to WO07/090773 (see passage from page 21, line 12, to page 26, line 17) or WO06/097419 (see passage from page 41 line 12 to page 44 line 10, and page 45, lines 15 to 34); the passages from the latter 2 documents mentioned are hereby incorporated by reference.

In general, the dibenzofurane moieties of the present polymers are attached as a side chain to the polymer's main chain. This architecture brings about some advantages, e.g. in the synthesis of the compounds since it opens the possibility to attach the desired functionality via grafting reactions, and simplifies certain in situ formations of the desired polymers, e.g. by coating the substrate with a suitable monomer mixture, with or without addition of a photoinitiator, and polymerizing the mixture by exposure to radiation (e.g. UV, electron beam etc.) and/or temperature.

The present polymers may be linear or crosslinked. In the case of crosslinked polymers, a certain fraction of the monomers making up the present polymer are crosslinkers (crosslinking agents), usually containing 2 or more polymerizable groups.

The invention thus includes a polymer which is obtainable by homopolymerization of a compound of the formula II

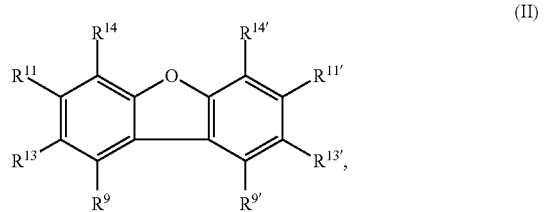

wherein
one of $R^9$, $R^{9'}$, $R^{11}$, $R^{11'}$, $R^{13}$, $R^{14}$, $R^{13'}$ and $R^{14'}$ is $R^{10'}$, which is a group —$(Sp)_{x10}$-[PG], PG is a polymerisable group, especially selected from vinyl, allyl, 1-methylvinyl, (meth)acryloyl, vinylphenyl, oxiranyl, glycidyl, oxetanyl, dimethylmaleimidyl;
x10 is 0 or 1;
$R^9$, $R^{9'}$ are further selected from H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, SiRR'R'', GeRR'R'', POAr$_2$, PAr$_2$, —CO—$R^{28}$;
$R^{11}$ and $R^{11'}$ are further selected from hydrogen, halogen, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, CN, —CO—$R^{28}$, SiRR'R'', GeRR'R'', POAr$_2$, PAr$_2$;
$R^{13}$, $R^{14}$, $R^{13'}$ and $R^{14'}$ are further selected from H, halogen, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, —CO—$R^{28}$, and $R^{13}$, $R^{14}$, $R^{13'}$ and $R^{14'}$ may also be SiRR'R'', GeRR'R'', POAr$_2$, PAr$_2$; or two substituents $R^9$, $R^{11}$, $R^{13}$, $R^{14}$, $R^{9'}$, $R^{11'}$, $R^{13'}$ and $R^{14'}$, which are adjacent to each other, together form a group

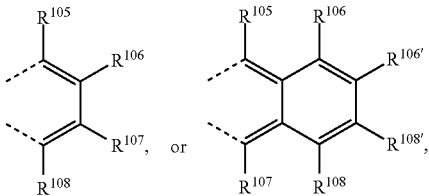

and all other symbols are as defined above.

Preferred polymers of the present invention have a glass transition temperature above 100° C.

Another aspect of this invention is related to polymer blends containing 1 to 99 percent of at least one polymer of the invention. The remainder 1 to 99 percent of the blend is composed of one or more polymeric materials selected from among chain growth polymers such as polystyrene, polybutadiene, poly(methyl methacrylate), and poly(ethylene oxide); step-growth polymers such as phenoxy resins, polycarbonates, polyamides, polyesters, polyurethanes, and polyimides; and crosslinked polymers such as crosslinked epoxy resins, crosslinked phenolic resins, crosslinked acrylate resins, and crosslinked urethane resins. Examples of these polymers may be found in Preparative Methods of Polymer Chemistry, W. R. Sorenson and T. W. Campbell, Second Edition, Interscience Publishers (1968). Also may be used in the blends are conjugated polymers such as poly(phenylene vinylene), substituted poly(phenylene vinylene)s, substituted polyphenylenes and polythiophenes. Examples of these conjugated polymers are given by Greenham and Friend in Solid State Physics, Vol. 49, pp. 1-149 (1995).

The electroluminescent material comprising a homopolymer as defined above further contains a luminiscent component, which is usually selected from phosphorescent metal complexes ("triplett emitters") and fluorescent dopants. It often contains one or more additional component(s), especially selected from electron transporters, hole transporters, inert polymers, viscosity modifiers, initiators, organic salts, and stabilizers such as antioxidants and UV absorbers.

Thus, the invention further pertains to electroluminescent materials containing at least one further component, especially selected from triplett emitters (TE), electron transporters, hole transporters, inert polymers (such as aromatic homo- or copolymers like polystyrene or further polymers listed above, e.g. as viscosity modifiers), initiators, organic salts (especially if soluble in the matrix, e.g. organic ammonium salts). The electroluminescent materials of the invention thus often contain 1 to 99 percent of at least one polymer of the invention, and 99 to 1 percent of one or more of the additional (auxiliary) components listed above, which often will make up the remainder of the material.

Monomers for the preparation of linear polymers usually contain only 1 class of polymerizable group and only 1 PG (i.e. one group $R^{10}$) per monomer unit, or for grafting one or more further class(es) of PGs. For crosslinking and/or in situ preparation of the polymer, monomers containing 2 or more groups PG (i.e. 2 or more groups $R^{10}$) of the same type may be used.

The polymers of this invention preferably have a weight average molecular weight of 2,000 Daltons or greater, especially 2,000 to 1,000,000 Daltons, more preferably 10,000 to 1,000,000 and most preferably 20,000 to 500,000 Daltons. Molecular weights are determined according to gel permeation chromatography using polystyrene standards and/or light scattering detectors.

The polymers of the invention may be prepared following techniques known in the art, e.g. for preparing linear or crosslinked polymers by condensation and/or addition polymerization methods. In many cases, a basic polymer network is formed by addition polymerization of suitable monomers containing ethylenically unsaturated moieties as PGs, e.g. by radical copolymerization using chemical radical starters, photoinitiators, actinic radiation and/or heat for the generation of radicals and initiation of the reaction. (Co)polymers formed in a first preparation step may be further modified e.g. by grafting one or more further monomers and/or functional groups on the polymer skeleton. Reaction conditions and methods may follow, for example, those described in WO06/097419 or WO07/090773. As mentioned above, the present polymers may also be formed in situ on the substrate, especially in the presence of crosslinkable monomers as described above. For example, the in situ polymerization may effectively be carried out using monomers containing an ethylenically unsaturated group PG, with a certain fraction or all (e.g. 1-100%) monomers carrying 2 or 3 groups PG of this type, and irradiating the monomers with actinic radiation (such as UV or electron beam; in case of UV radiation occasionally in presence of a photoinitiator).

Preferred polymers of the formula I present in the materials of the invention are those wherein $R^9$, $R^{9'}$ are selected from H, $C_1$-$C_{18}$alkyl, $C_3$-$C_{12}$cycloalkyl, halogen, $R^{10}$, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, SiRR'R", GeRR'R", POAr$_2$, PAr$_2$, or is —CO—$R^{28}$;

$R^{11}$ and $R^{11'}$ are selected from hydrogen, halogen, especially fluorine, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $R^{10}$, $C_2$-$C_{18}$alkynyl, $C_1$-$C_{18}$alkoxy, $C_1$-$C_{18}$alkoxy which is substituted by E and/or interrupted by D, CN, or —CO—$R^{28}$, SiRR'R", GeRR'R", POAr$_2$, PAr$_2$;

$R^{13}$, $R^{14}$, $R^{13'}$ and $R^{14'}$ are selected from H, halogen, especially fluorine, $C_1$-$C_{18}$alkyl, $R^{10}$, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN or —CO—$R^{28}$, and $R^{13}$, $R^{14}$, $R^{13'}$ and $R^{14'}$ may also be SiRR'R", GeRR'R", POAr$_2$, PAr$_2$;

or two substituents $R^9$, $R^{11}$, $R^{13}$, $R^{14}$, $R^{9'}$, $R^{11'}$, $R^{13'}$ and $R^{14'}$, which are adjacent to each other, together form a group

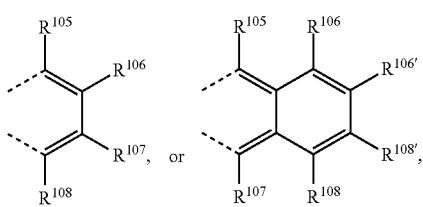

$R^{105}$, $R^{106}$, $R^{107}$, $R^{108}$, $R^{105'}$, $R^{106'}$, $R^{107'}$ and $R^{108'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, or $R^{10}$, D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—;

and

E is —OR$^{29}$; —SR$^{29}$; —NR$^{25}$R$^{26}$; —COR$^{28}$; —COOR$^{27}$; —CONR$^{25}$R$^{26}$; —CN; or halogen;

G is E, $C_1$-$C_{18}$alkyl, $C_3$-$C_{12}$cycloalkyl, $C_2$-$C_{18}$alkyl which is interrupted by D, $C_1$-$C_{18}$perfluoroalkyl, or $C_1$-$C_{18}$alkoxy which is substituted by E and/or interrupted by D, wherein $R^{23}$, $R^{24}$, $R^{25}$ and $R^{26}$ are independently of each other H; $C_6$-$C_{18}$aryl; $C_6$-$C_{18}$arylalkyl; $C_3$-$C_{12}$cycloalkyl; $C_6$-$C_{18}$aryl or $C_6$-$C_{18}$arylalkyl which is substituted by $C_1$-$C_{18}$alkyl and/or $C_1$-$C_{18}$alkoxy; $C_1$-$C_{18}$alkyl; or $C_2$-$C_{18}$alkyl which is interrupted by —O—; or $R^{25}$ and $R^{26}$ together form a five or six membered ring, in particular

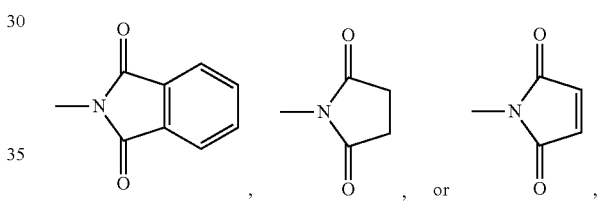

$R^{27}$ and $R^{28}$ are independently of each other H; $C_6$-$C_{18}$aryl; $C_6$-$C_{18}$arylalkyl; $C_6$-$C_{18}$aryl or $C_6$-$C_{18}$arylalkyl which is substituted by $C_1$-$C_{18}$alkyl and/or $C_1$-$C_{18}$alkoxy; $C_1$-$C_{18}$alkyl; $C_3$-$C_{12}$cycloalkyl; or $C_2$-$C_{18}$alkyl which is interrupted by —O—;

$R^{29}$ is H; $C_6$-$C_{18}$aryl; $C_6$-$C_{18}$arylalkyl; $C_6$-$C_{18}$aryl or $C_6$-$C_{18}$arylalkyl which is substituted by $C_1$-$C_{18}$alkyl and/or $C_1$-$C_{18}$alkoxy; $C_1$-$C_{18}$alkyl; $C_2$-$C_{18}$alkylcarbonyl; $C_3$-$C_{12}$cycloalkyl; or $C_2$-$C_{18}$alkyl or $C_2$-$C_{18}$alkylcarbonyl which is interrupted by —O—;

$R^{30}$ and $R^{31}$ are independently of each other $C_1$-$C_{18}$alkyl, $C_3$-$C_{12}$cycloalkyl, $C_6$-$C_{18}$aryl, or $C_6$-$C_{18}$aryl, which is substituted by $C_1$-$C_{18}$alkyl, and $R^{32}$ is $C_1$-$C_{18}$alkyl, $C_6$-$C_{18}$aryl, or $C_6$-$C_{18}$aryl, which is substituted by $C_1$-$C_{18}$alkyl, R, R' and R" independently are selected from $C_1$-$C_{12}$alkyl, $C_1$-$C_{12}$haloalkyl, $C_5$-$C_{10}$aryl, $C_3$-$C_{12}$cycloalkyl, preferably from $C_1$-$C_6$alkyl, phenyl, cyclopentyl, cyclohexyl; and Ar independently is selected from $C_5$-$C_{10}$aryl, or $C_5$-$C_{10}$aryl which is substituted by $C_1$-$C_{18}$alkyl;

where formula I contains one group $R^{10}$, and $R^{10}$ group —(Sp)$_{x10}$-[PG']<, wherein Sp is a divalent organic spacer, PG' is a group derived from a polymerisable group, and x10 is 0 or 1.

For example, the electroluminescent material of the invention may comprise a polymer of the formula III

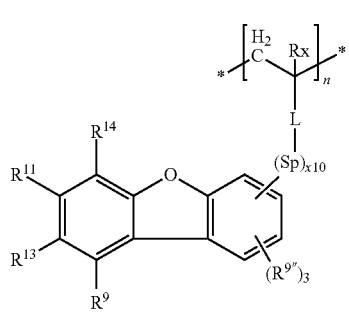
(III)

wherein n ranges from 2 to 10000;

L is $CH_2$, CO or a direct bond;

$R^9$, $R^{11}$, $R^{13}$, $R^{14}$, are selected from H, $C_1$-$C_{18}$alkyl, halogen, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, SiRR'R", GeRR'R", $POAr_2$, $PAr_2$, or is —CO—$R^{28}$;

each of the residues $R^{9'''}$ is independently selected from those defined for $R^9$, Rx is H or methyl and all other symbols are as defined above;

preferred materials of this class comprise a polymer of the formula III, wherein n ranges from 5 to 5000, especially 10 to 1000;

x10 is 0;

$R^9$, $R^{9'''}$, $R^{11}$, $R^{13}$, $R^{14}$, are selected from H, $C_1$-$C_8$alkyl, fluoro, $C_1$-$C_8$alkyl which is substituted by E, $C_2$-$C_{18}$alkyl which is interrupted by D, phenyl, phenyl which is substituted by G, $C_4$-$C_{18}$heteroaryl, $C_4$-$C_{18}$heteroaryl which is substituted by G, $C_2$-$C_8$alkenyl, $C_2$-$C_8$alkynyl, $C_1$-$C_8$alkoxy, $C_1$-$C_8$alkoxy which is substituted by E, $C_2$-$C_{18}$alkoxy which is interrupted by D, $C_7$-$C_{25}$phenylalkyl, SiRR'R", GeRR'R", $POAr_2$, $PAr_2$, or is —CO—$R^{28}$;

D is —CO—; —COO—; —S—; —SO—; —$SO_2$—; —O—; —$NR^{25}$—; —$SiR^{30}R^{31}$—; —$POR^{32}$—; and E is —$OR^{29}$; —$NR^{25}R^{26}$; —$COR^{28}$; —$COOR^{27}$; —$CONR^{25}R^{26}$; —CN; or halogen;

G is E, $C_1$-$C_8$alkyl, cyclohexyl, $C_2$-$C_{18}$alkyl which is interrupted by D, $C_1$-$C_8$perfluoroalkyl, $C_1$-$C_{18}$alkoxy which is substituted by E, $C_2$-$C_{18}$alkoxy which is interrupted by D, wherein $R^{25}$ and $R^{26}$ are independently of each other H; phenyl; $C_7$-$C_{12}$phenylalkyl; cyclohexyl; phenyl or $C_7$-$C_{12}$phenylalkyl which is substituted by $C_1$-$C_8$alkyl or $C_1$-$C_8$alkoxy; $C_1$-$C_8$alkyl; or $C_2$-$C_{18}$alkyl which is interrupted by —O—; or $R^{25}$ and $R^{26}$ together form a five or six membered ring selected from

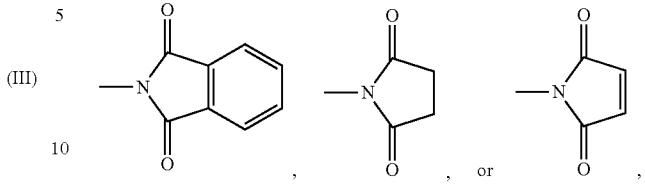

$R^{27}$ and $R^{28}$ are independently of each other H; phenyl; $C_7$-$C_{12}$phenylalkyl; phenyl or $C_7$-$C_{12}$phenylalkyl which is substituted by $C_1$-$C_8$alkyl and/or $C_1$-$C_8$alkoxy; $C_1$-$C_8$alkyl; cyclohexyl; or $C_2$-$C_{18}$alkyl which is interrupted by —O—;

$R^{29}$ is H; phenyl; $C_7$-$C_{12}$phenylalkyl; phenyl or $C_7$-$C_{12}$phenylalkyl which is substituted by $C_1$-$C_8$alkyl and/or $C_1$-$C_8$alkoxy; $C_1$-$C_8$alkyl; $C_2$-$C_8$alkylcarbonyl; cyclohexyl; or $C_2$-$C_{18}$alkyl or $C_2$-$C_{18}$alkylcarbonyl which is interrupted by —O—;

$R^{30}$ and $R^{31}$ are independently of each other $C_1$-$C_8$alkyl, phenyl, or phenyl which is substituted by $C_1$-$C_8$alkyl, and $R^{32}$ is $C_1$-$C_8$alkyl, phenyl, or phenyl which is substituted by $C_1$-$C_8$alkyl, R, R' and R" independently are selected from $C_1$-$C_6$alkyl, phenyl, cyclopentyl, cyclohexyl; and Ar is phenyl or phenyl substituted by $C_1$-$C_8$alkyl.

Asterisks in formula III indicate the progression of the polymer chain, with common end groups usually selected from hydrogen, alkyl (e.g. $C_1$-$C_8$), aryl (e.g. phenyl) or arylalkyl (e.g. benzyl) as defined above and/or chain termination agents, or "unreacted", single bonded monomer units IV:

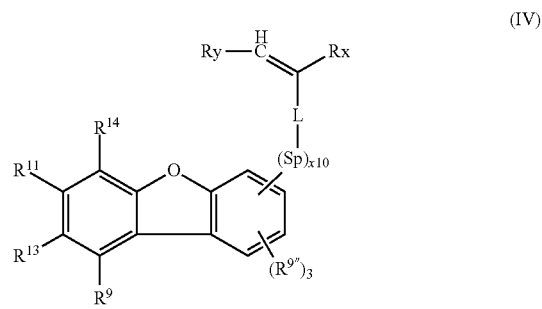
(IV)

where Rx is H or methyl and Ry is the bond to the polymer chain, or Ry is H or methyl and Rx is the bond to the polymer chain, and all other symbols are as defined above.

Generally preferred electroluminescent material according to the invention comprise a polymer containing 10 to 1000 structural units of the formula I or III, wherein x10 is 0;

any of $R^9$, $R^{9'}$ $R^{9'''}$, $R^{11}$, $R^{13}$, $R^{14}$, $R^{11'}$, $R^{13'}$, $R^{14'}$ independently is selected from H, $C_1$-$C_8$alkyl, fluoro, $C_1$-$C_8$alkyl which is substituted by E, $C_2$-$C_{18}$alkyl which is interrupted by D, phenyl, phenyl which is substituted by G, $C_4$-$C_{18}$heteroaryl, $C_4$-$C_{18}$heteroaryl which is substituted by G, $C_2$-$C_8$alkenyl, $C_2$-$C_8$alkynyl, $C_1$-$C_8$alkoxy, $C_1$-$C_8$alkoxy which is substituted by E, $C_2$-$C_{18}$alkoxy which is interrupted by D, $C_7$-$C_{25}$phenylalkyl, SiRR'R", GeRR'R", $POAr_2$, $PAr_2$, or is —CO—$R^{28}$;

D is —CO—; —COO—; —O—; —NR$^{25}$—; —SiR$^{30}$R$^{31}$—; and

E is —OR$^{29}$; —NR$^{25}$R$^{26}$; —COR$^{28}$; —COOR$^{27}$; —CONR$^{25}$R$^{26}$; or fluoro;

G is E or C$_1$-C$_8$alkyl;

R$^{25}$ and R$^{26}$ are independently of each other H; C$_1$-C$_8$alkyl; cyclohexyl;

R$^{27}$ and R$^{28}$ are independently of each other H; phenyl; benzyl; phenyl or benzyl which is substituted by C$_1$-C$_8$alkyl and/or C$_1$-C$_8$alkoxy; C$_1$-C$_8$alkyl;

R$^{29}$ is H; phenyl; benzyl; phenyl or benzyl which is substituted by C$_1$-C$_8$alkyl and/or C$_1$-C$_8$alkoxy; C$_1$-C$_8$alkyl; acetyl; cyclohexyl; or C$_2$-C$_{12}$alkyl which is interrupted by —O—;

R$^{30}$ and R$^{31}$ are independently of each other methyl or phenyl, and

R, R' and R" independently are selected from methyl, ethyl, phenyl; and

Ar is phenyl;

especially where any of R$^9$, R$^{9'}$ R$^{9'''}$, R$^{11}$, R$^{13}$, R$^{14}$, R$^{11'}$, R$^{13'}$, R$^{14'}$ independently is selected from H, C$_1$-C$_8$alkyl, SiRR'R".

The present invention further pertains to novel polymers, i.e. a homopolymer of the formula III'

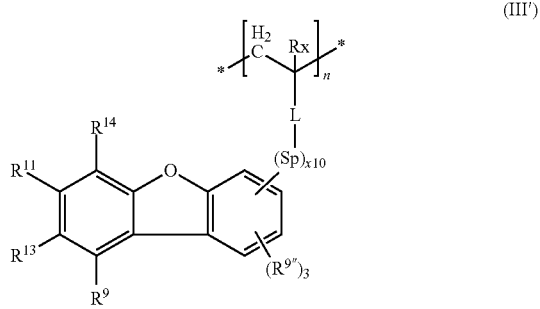

(III')

wherein n ranges from 5 to 10000;

at least one of the residues R$^9$, R$^{9'''}$, R$^{11}$, R$^{13}$, R$^{14}$ is selected from C$_1$-C$_{18}$alkyl, halogen, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$aralkyl, SiRR'R", GeRR'R", POAr$_2$, PAr$_2$, CO—R$^{28}$;

especially from halogen, C$_2$-C$_{18}$alkynyl, C$_1$-C$_{18}$alkoxy, SiRR'R", GeRR'R", POAr$_2$, PAr$_2$; while the remaining residues may also be hydrogen;

D is —CO—; —COO—; —S—; —SO—; —SO$_2$—; —O—; —NR$^{25}$—; —SiR$^{30}$R$^{31}$—; —POR$^{32}$—; and E is —OR$^{29}$; —NR$^{25}$R$^{26}$; —COR$^{28}$; —COOR$^{27}$; —CONR$^{25}$R$^{26}$; —CN; or halogen;

G is E, C$_1$-C$_8$alkyl, cyclohexyl, C$_2$-C$_{18}$alkyl which is interrupted by D, C$_1$-C$_8$perfluoroalkyl, C$_1$-C$_{18}$alkoxy which is substituted by E, C$_2$-C$_{18}$alkoxy which is interrupted by D, wherein R$^{25}$ and R$^{26}$ are independently of each other H; phenyl; C$_7$-C$_{12}$phenylalkyl; cyclohexyl; phenyl or C$_7$-C$_{12}$phenylalkyl which is substituted by C$_1$-C$_8$alkyl or C$_1$-C$_8$alkoxy; C$_1$-C$_{18}$alkyl; or C$_2$-C$_{18}$alkyl which is interrupted by —O—; or R$^{25}$ and R$^{26}$ together form a five or six membered ring selected from

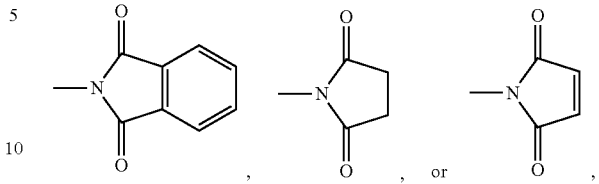

R$^{27}$ and R$^{28}$ are independently of each other H; phenyl; C$_7$-C$_{12}$phenylalkyl; phenyl or C$_7$-C$_{12}$phenylalkyl which is substituted by C$_1$-C$_8$alkyl and/or C$_1$-C$_8$alkoxy; C$_1$-C$_8$alkyl; cyclohexyl; or C$_2$-C$_{18}$alkyl which is interrupted by —O—;

R$^{29}$ is H; phenyl; C$_7$-C$_{12}$phenylalkyl; phenyl or C$_7$-C$_{12}$phenylalkyl which is substituted by C$_1$-C$_8$alkyl and/or C$_1$-C$_8$alkoxy; C$_1$-C$_8$alkyl; C$_2$-C$_8$alkylcarbonyl; cyclohexyl; or C$_2$-C$_{18}$alkyl or C$_2$-C$_{18}$alkylcarbonyl which is interrupted by —O—;

R$^{30}$ and R$^{31}$ are independently of each other C$_1$-C$_8$alkyl, phenyl, or phenyl which is substituted by C$_1$-C$_8$alkyl, and R$^{32}$ is C$_1$-C$_8$alkyl, phenyl, or phenyl which is substituted by C$_1$-C$_8$alkyl, R, R' and R" independently are selected from C$_1$-C$_6$alkyl, phenyl, cyclopentyl, cyclohexyl; and Ar is phenyl or phenyl substituted by C$_1$-C$_8$alkyl;

L is CH$_2$, CO or a direct bond; Rx is H or methyl;

x10 is 0 or 1 and Sp is O, C$_1$-C$_4$alkylene-O, CH$_2$—CHOH—CH$_2$—O, COO, CONR22, C$_1$-C$_4$alkylene, or CH$_2$CHOHCH$_2$.

Preferred variants and substitution patterns of the novel polymers, as well as the method for preparation, are mainly as described further above for the polymers used in the electroluminescent material of the invention.

Some valuable monomers for the preparation of the present polymers are novel compounds, which are of the formula V

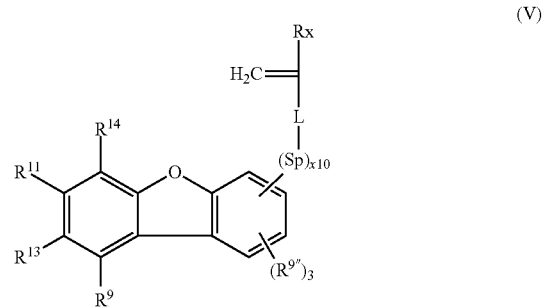

(V)

wherein at least one of the residues R$^9$, R$^{9'''}$, R$^{11}$, R$^{13}$, R$^{14}$ is selected from halogen such as iodo, C$_2$-C$_{18}$alkynyl, C$_1$-C$_{18}$alkoxy, SiRR'R", GeRR'R", POAr$_2$, PAr$_2$; while the remaining residues may also be hydrogen;

R, R' and R" independently are selected from C$_1$-C$_6$alkyl, phenyl, cyclopentyl, cyclohexyl; and Ar is phenyl or phenyl substituted by C$_1$-C$_8$alkyl;

L is CH$_2$, CO or a direct bond; Rx is H or methyl;

x10 is 0 or 1 and Sp is O, C$_1$-C$_4$alkylene-O, CH$_2$—CHOH—CH$_2$—O, COO, CONR22, C$_1$-C$_4$alkylene, or CH$_2$CHOHCH$_2$.

Each of the residues $R^{9'''}$, as present e.g. in formulae III, III', IV and V, is selected independently from the meanings indicated, the residues thus may be identical or differ from each other.

The preparation of the monomers for the present polymeric compounds may follow methods known in the art, e.g. as described in the literature initially cited. The introduction of the polymerizable group may be completed before a further derivatization of the monomer by introduction of any further substituent $R^9$, $R^{9'''}$, $R^{11}$, $R^{13}$, $R^{14}$; in many cases, however, a compound containing a substituent $R^9$, $R^{9'''}$, $R^{11}$, $R^{13}$, $R^{14}$ is provided first, and this product is then converted in a second step into the monomer containing the polymerizable group PG. Substituents may also be modified in subsequent steps, e.g. after first introduction of a reactive substituent such as halogen, haloalkyl, hydroxy or hydroxyalkyl.

Reaction conditions are adapted according to methods known in the art, including, but not limited to, use of solvents, temperatures, catalysts, protective measures, workup, isolation and purification procedures. Further details are explained in the present examples.

The present invention is also directed to an electronic device comprising the present polymer and its fabrication process. The electronic device can comprise at least one organic active material positioned between two electrical contact layers, wherein at least one of the layers of the device includes the light emitting dopant compound, which may be a phosphorescent dopant (usually a metal complex such as an Ir based triplett emitter, or a fluorescent compound). The electronic device can comprise an anode layer (a), a cathode layer (e), and an active layer (c). Adjacent to the anode layer (a) is an optional hole-injecting/transport (electron blocking) layer (b), and adjacent to the cathode layer (e) is an optional electron-injection/transport (hole blocking) layer (d). Layers (b) and (d) are examples of charge transport layers.

The active layer (c) preferably comprises at least approximately 0.1 weight percent of the luminescent dopant (often more than 1%, or 0.1 to 10%).

The device may include a support or substrate adjacent to the anode layer (a) or the cathode layer (e). Most frequently, the support is adjacent the anode layer (a). The support can be flexible or rigid, organic or inorganic. Generally, glass or flexible organic films are used as a support. The anode layer (a) is an electrode that is more efficient for injecting holes compared to the cathode layer (e). The anode can include materials containing a metal, mixed metal, alloy, metal oxide or mixed-metal oxide. Suitable metal elements within the anode layer (a) can include the Groups 4, 5, 6, and 8-11 transition metals. If the anode layer (a) is to be light transmitting, mixed-metal oxides of Groups 12, 13 and 14 metals, such as indium-tin-oxide, may be used. Some non-limiting, specific examples of materials for anode layer (a) include indium-tin-oxide ("ITO"), aluminum-tin-oxide, gold, silver, copper, nickel, and selenium.

The anode layer (a) may be formed by a chemical or physical vapor deposition process or spin-cast process, inject or gravure printing process. Chemical vapor deposition may be performed as a plasma-enhanced chemical vapor deposition ("PECVD") or metal organic chemical vapor deposition ("MOCVD").

Physical vapor deposition can include all forms of sputtering (e.g., ion beam sputtering), e-beam evaporation, and resistance evaporation.

Specific forms of physical vapor deposition include rf magnetron sputtering or inductively-coupled plasma physical vapor deposition ("ICP-PVD"). These deposition techniques are well-known within the semiconductor fabrication arts.

A hole-transport layer (b) may be adjacent to the anode; this layer may be split into a hole injecting (b1) and a hole transporting (b2) layer. Hole transporting small molecule compounds as well as polymers can be used.

Commonly used hole transporting molecules include: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis (9H-carbazol-9-yl)cyclobutane (DCZB), N,N,N',N'-tetrakis (4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), N,N'-Di(naphthalen-1-yl)-N,N'-diphenyl-benzidine (NPD), 1,3-bis(9-carbazolyl)benzene (mCP), porphyrinic compounds, phthalocyanines, and combinations thereof. Further materials and methods of use in this regard may be as described in US-A-2007-0087219 (see sections [0096]-[0154] therein), which passages are hereby incorporated by reference.

Commonly used hole transporting polymers are polyvinylcarbazole, (phenylmethyl) polysilane, poly(3,4-ethylendioxythiophene) (PEDOT), triarylamine polymers (such as poly [(9,9-dioctylfluorenyl-2,7-diyl)-co-(4,4'-(N-(4-sec-butylphenyl))diphenylamine)] [TFB]), polypyrrole, and polyaniline. Hole-transporting polymers can be obtained by doping hole-transporting molecules such as those mentioned above into polymers such as polystyrene and polycarbonate.

The hole-injection/transport layer (b) can be formed using any conventional means, including spin-coating, casting, and printing, such as gravure printing. The layer can also be applied by ink jet printing, thermal patterning, or chemical or physical vapor deposition.

Usually, the anode layer (a) and the hole-injection/transport layer (b), if present, are patterned during the same lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet-chemical or dry-etching techniques. Other processes for patterning that are well known in the art can also be used. When the electronic devices are located within an array, the anode layer (a) and hole injection/transport layer (b) typically are formed into substantially parallel strips having lengths that extend in substantially the same direction. Layer (b) can be crosslinked.

The active layer (c) comprises the luminescent dopant and the polymer of the present invention. The particular material chosen may depend on the specific application, potentials used during operation, or other factors. The active layer (c) may comprise a further host material capable of transporting electrons and/or holes, doped with an emissive material that may trap electrons, holes, and/or excitons, such that excitons relax from the emissive material via a photoemissive mechanism. Active layer (c) may comprise a single material that combines transport and emissive properties. Whether the emissive material is a dopant or a major constituent, the active layer may comprise other materials, such as dopants that tune the emission of the emissive material. Active layer (c) may include a plurality of emissive materials capable of, in combination, emitting a desired spectrum of light. Examples of emissive materials include the phosphorescent metal compounds disclosed in WO06000544, WO06067074, WO07074093, and publications cited therein; as well as certain fluorescent polyaryls as disclosed e.g. in EP-A-1138746, EP-A-1245659. Examples of fluorescent emissive materials include DCM and DMQA. Examples of further host materials include $Alq_3$, CBP and mCP. Examples of emissive and host materials are disclosed in U.S. Pat. No. 6,303,238 B, which is incorporated by reference in its entirety.

Examples of methods for forming the active layer (c) include deposition by solution processing. Examples of film-forming methods from a solution include application methods, such as spin-coating, casting, microgravure coating, roll-coating, wire bar-coating, dip-coating, spray-coating, screen-printing, flexography, offset-printing, gravure printing and ink-jet-printing.

As the composition used for forming the active layer (c) at least one kind of present polymers, a light emitting compound and at least one solvent are contained, and additives, such as hole transport material, electron transport material, luminescent material, rheology modifier or stabilizer, may be added. The amount of solvent in the composition is 1 to 99 wt % of the total weight of the composition and preferably 60 to 99 wt % and more preferably 80 to 99 wt %.

The solvent used in the solution processing method is not particularly limited and preferable are those which can dissolve or uniformly disperse the materials. Preferably the materials may be dissolved in a solvent, the solution deposited onto a substrate, and the solvent removed to leave a solid film. Any suitable solvents may be used to dissolve the compounds, provided it is inert, may dissolve at least some material and may be removed from the substrate by conventional drying means (e.g. application of heat, reduced pressure, airflow, etc.). Suitable organic solvents include, but are not limited to, are aromatic or aliphatic hydrocarbons, halogenated such as chlorinated hydrocarbons, esters, ethers, ketones, amide, such as chloroform, dichloroethane, tetrahydrofuran, toluene, xylene, ethyl acetate, butyl acetate, methyl ethyl ketone, acetone, dimethyl formamide, dichlorobenzene, chlorobenzene, propylene glycol monomethyl ether acetate (PGMEA), and alcohols, and mixtures thereof. Also water and mixtures with water miscible solvents are possible. Layer (c) can be crosslinked.

Optional layer (d) can function both to facilitate electron injection/transport, hole blocking, and also serve as a buffer layer or confinement layer to prevent quenching reactions at layer interfaces. More specifically, layer (d) may promote electron mobility and reduce the likelihood of a quenching reaction if layers (c) and (e) would otherwise be in direct contact. Examples of materials for optional layer (d) include metal-chelated oxinoid compounds (e.g., tris(8-hydroxyquinolato)aluminum ($Alq_3$) or the like); phenanthroline-based compounds (e.g., 2,9-dimethyl-4,7-diphenyl-1,10-phenanthroline ("DDPA"), 4,7-diphenyl-1,10-phenanthroline ("DPA"), or the like; azole compounds (e.g., 2-(4-biphenylyl)-5-(4-t-butylphenyl)-1,3,4-oxadiazole ("PBD") or the like, 3-(4-biphenylyl)-4-phenyl-5-(4-t-butylphenyl)-1,2,4-triazole ("TAZ") or the like; other similar compounds; or any one or more combinations thereof. Further materials and methods of use in this regard may be as described in US-A-2006-0210830 (see sections [0076]-[0079] therein), and in US-A-2007-0042220 (see sections [0110]-[0114] therein), which passages are hereby incorporated by reference. Alternatively, optional layer (d) may be inorganic and comprise BaO, LiF, $Li_2O$, or the like. Layer (d) can be crosslinked.

The electron injection/transport layer (d) can be formed using any conventional means, including spin-coating, casting, and printing, such as gravure printing. The layer can also be applied by ink jet printing, thermal patterning, or chemical or physical vapor deposition.

The cathode layer (e) is an electrode that is particularly efficient for injecting electrons or negative charge carriers. The cathode layer (e) can be any metal or nonmetal having a lower work function than the first electrical contact layer (in this case, the anode layer (a)). Materials for the second electrical contact layer can be selected from alkali metals of Group 1 (e.g., Li, Na, K, Rb, Cs), the Group 2 (alkaline earth) metals, the Group 12 metals, the rare earths, the lanthanides (e.g., Ce, Sm, Eu, or the like), and the actinides. Materials, such as aluminum, indium, calcium, barium, yttrium, and magnesium, and combinations thereof, may also be used. Li-containing organometallic compounds, LiF, and $Li_2O$ can also be deposited between the organic layer and the cathode layer to lower the operating voltage. Specific non-limiting examples of materials for the cathode layer (e) include barium, lithium, cerium, cesium, europium, rubidium, yttrium, magnesium, or samarium.

The cathode layer (e) is usually formed by a chemical or physical vapor deposition process. In general, the cathode layer will be patterned, as discussed above in reference to the anode layer (a) and optional hole injecting layer (b). If the device lies within an array, the cathode layer (e) may be patterned into substantially parallel strips, where the lengths of the cathode layer strips extend in substantially the same direction and substantially perpendicular to the lengths of the anode layer strips.

Electronic elements called pixels are formed at the cross points (where an anode layer strip intersects a cathode layer strip when the array is seen from a plan or top view).

In other embodiments, additional layer(s) may be present within organic electronic devices. For example, a layer between the hole injecting layer (b) and the active layer (c) may facilitate positive charge transport, band-gap matching of the layers, function as a protective layer, or the like. Similarly, additional layers between the electron injecting layer (d) and the cathode layer (e) may facilitate negative charge transport, band-gap matching between the layers, function as a protective layer, or the like. Layers that are known in the art generally may be used. Some or all of the layers may be surface treated to increase charge carrier transport efficiency. The choice of materials for each of the component layers may be determined by balancing the goals of providing a device with high device efficiency with the cost of manufacturing, manufacturing complexities, or potentially other factors.

The materials of the charge transport layers (b) and (d) often are of the same type as the materials of the active layer (c). More specifically, if the active layer (c) comprises a small molecule compound, then the charge transport layers (b) and (d), if either or both are present, often comprises a different small molecule compound. If the active layer (c) contains a polymer, the charge transport layers (b) and (d), if either or both are present, often contain a polymer, too. Still, the active layer (c) may contain a small molecule compound, and any of its adjacent layers (e.g. charge transport layers) may be polymers.

Each functional layer may be made up of more than one layer. For example, the cathode layer may comprise a layer of a Group I metal and a layer of aluminum. The Group I metal may lie closer to the active layer (c), and the aluminum may help to protect the Group I metal from environmental contaminants, such as water.

Although not meant to limit, the different layers may have the following range of thicknesses: inorganic anode layer (a), usually no greater than approximately 500 nm, for example, approximately 50-200 nm; optional hole-injecting layer (b), usually no greater than approximately 100 nm, for example, approximately 50-200 nm; active layer (c), usually no greater than approximately 100 nm, for example, approximately 10-80 nm; optional electron-injecting layer (d), usually no greater than approximately 100 nm, for example, approximately 10-80 nm; and cathode layer (e), usually no greater than approximately 1000 nm, for example, approximately 30-500 nm. If the anode layer (a) or the cathode layer (e) needs to transmit at least some light, the thickness of such layer may not exceed approximately 100 nm.

The location of the electron-hole recombination zone in the device, and thus the emission spectrum of the device, can be affected by the relative thickness of each layer. Thus, the thickness of the electron-transport layer should be chosen so that the electron-hole recombination zone lies within the light-emitting layer (i.e., active layer (c)). The desired ratio of layer thicknesses can depend on the exact nature of the materials used.

The efficiency of the devices made with metal complexes can be further improved by optimizing the other layers in the device. For example, more efficient cathodes such as Ca, Ba, Mg/Ag, or LiF/Al can be used. Shaped substrates and hole transport materials that result in a reduction in operating voltage or increase quantum efficiency are also applicable. Additional layers can also be added to tailor the energy levels of the various layers and facilitate electroluminescence.

Depending upon the application of the electronic device, the active layer (c) can be a light-emitting layer that is activated by a signal (such as in a light-emitting diode) or a layer of material that responds to radiant energy and generates a signal with or without an applied potential (such as detectors or voltaic cells). Examples of electronic devices that may respond to radiant energy are selected from photoconductive cells, photoresistors, photoswitches, phototransistors, and phototubes, and photovoltaic cells. Persons skilled in the art are capable of selecting material(s) suitable for their particular application(s).

The electroluminescent devices may be employed for full color display panels in, for example, mobile phones, televisions and personal computer screens. Accordingly the present invention relates also to a device selected from stationary and mobile displays, such as displays for computers, mobile phones, laptops, pdas, TV sets, displays in printers, kitchen equipment, billboards, lightings, information boards and destination boards in trains and buses, containing an organic light emitting diode according to the present invention.

In OLEDs, electrons and holes, injected from the cathode (e) and anode (a) layers, respectively, into the photoactive layer (c), form negative and positively charged polarons in the active layer (c). These polarons migrate under the influence of the applied electric field, forming a polaron exciton with an oppositely charged species and subsequently undergoing radiative recombination. A sufficient potential difference between the anode and cathode, usually less than approximately 20 volts, and in some instances no greater than approximately 5 volts, may be applied to the device. The actual potential difference may depend on the use of the device in a larger electronic component. In many embodiments, the anode layer (a) is biased to a positive voltage and the cathode layer (e) is at substantially ground potential or zero volts during the operation of the electronic device. A battery or other power source (s) may be electrically connected to the electronic device as part of a circuit.

The compound does not need to be in a solid matrix diluent (e.g., host charge transport material) when used in layer (b) (c), or (d) in order to be effective. A layer greater than approximately 1% by weight of the metal complex compound, based on the total weight of the layer, and up to substantially 100% of the present polymer can be used as the active layer (c). Additional materials can be present in the active layer (c) with the complex compound. For example, a fluorescent dye may be present to alter the color of emission.

A diluent may also be added. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the present polymer is generally present in a small amount, usually less than 20% by weight, preferably less than 10% by weight, based on the total weight of the layer.

The following test methods and examples are for illustrative purposes only and are not to be construed to limit the instant invention in any manner whatsoever. Room temperature (r.t.) depicts a temperature in the range 20-25° C.; over night denotes a time period in the range 12-16 hours. Percentages are by weight unless otherwise indicated.

Abbreviations used in the examples or elsewhere:
AIBN azo-bis-isobutyronitrile
CIE colour definition according to Commission Internationale de l'Eclairage
DMF dimethylformamide
EE ethyl acetate
EtOH ethanol
HMPTA hexamethylphosphorus triamide
Ir(ppy)$_3$ Iridium tris(2-phenylpyridine) (Baldo et al., Appl. Phys. Lett. 1999, 75, 4-6)
ITO indium tin oxide
$M_w$ molecular mass weight average
$M_n$ molecular mass number average
PBD 2-(p-tert.butylphenyl)-5-biphenylyl-1,3,4-oxadiazole
PDI polydispersity index (=ratio $[M_w]/[M_n]$)
PEDOT:PSS poly(3,4-ethylenedioxythiophene)poly(styrenesulfonate)
PG polymerizable group
QE quantum efficiency
TBME tert.-butyl methyl ether
THF tetrahydrofuran
TPD N,N'-biphenyl-N,N'-di-m-tolyl-benzidine Example 1

16.09 g (0.259 mol) of Potassium hydroxide (86%) are placed in a 500 ml three necked round bottomed flask equipped with a magnetic stirrer and a reflux condenser. 200 ml of THF and 6.5 ml of Dichloromethane are added. The mixture is refluxed. After 1 hour the mixture is cooled to room temperature. A solution of 8 g (37.74 mmol) dibenzofuran-4-boronic acid, 0.8 g (3.02 mmol) of Triphenylphosphine, 339 mg (0.7 mmol) of Palladium (II) acetate and 200 ml of Methanol are added. The reaction mixture is heated to 60° C. internal temperature. After 2 hours the reaction is complete and cooled down to room temperature. The mixture is diluted with H₂O and Ethylacetate. The organic phase is extracted twice with water and once with brine. The organic phase is dried over Sodiumsulfate and the solvent evaporated. The crude product is purified by column chromatography (Heptane). 4-Vinyl-dibenzofuran is isolated in 42% yield.

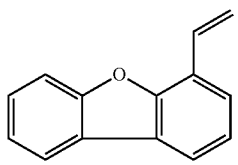

¹H-NMR (300 MHz, CDCl₃):
7.94 (d,1H)
7.84 (d, 1H)
7.61 (d, 1H)
7.50 (m, 2H)
7.36 (m, 2H)
7.12 (dxd 1H)
6.32 (d, 1H)
5.60 (d, 1H)

Example 2

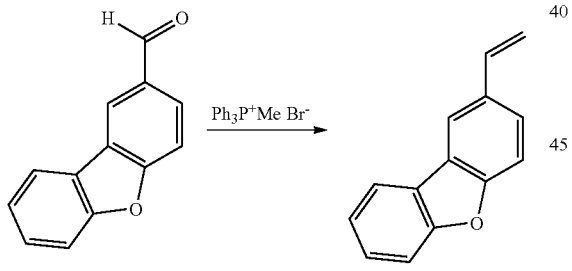

22.7 g (63.7 mmol) of Methyl triphenylphosphonium bromide and 200 ml of dry THF are placed in a dried 500 ml three necked round bottomed flask, equipped with a magnetic stirrer and the reaction mixture is cooled to 0° C. internal temperature with a NaCl/ice bath. 41.8 ml (66.9 mmol) of 1.6 M Butyl lithium solution in Hexane are added within 30 minutes while keeping the internal temperature below 3° C. The reaction mixture is stirred at the same temperature for 45 minutes, then 47.2 mmol of Dibenzofuran-2-carboxaldehyde dissolved in 100 ml of dry THF are added within 30 minutes. After two hours the reaction mixture is warmed to room temperature, added to 500 ml of water and extracted three times with 500 ml of Ethylacetate. The combined organic phases are washed once with 500 ml of a 1:1 mixture of buffer pH=1 and brine, once with 30 ml of brine, dried over Magnesiumsulfate, filtered and evaporated. The crude product is dissolved in Dichloromethane, 100 g of silica are added and the solvent is evaporated. The resulting powder is added on top of 300 g of silica in a sintered glass funnel and the product eluted with Hexane/Ethylacetate=8:1. The product is crystallized from 2-Propanol. 2-Vinyl-dibenzofuran is isolated in 95% yield.

¹H-NMR (300 MHz, CDCl₃):
7.94 (d, 1H)
7.98-7.92 (m, 2H)
7.64-7.32 (m, 5H)
6.92 (dxd 1H)
5.82 (d, 1H)
5.30 (d, 1H)

Example 3

Polymer 1

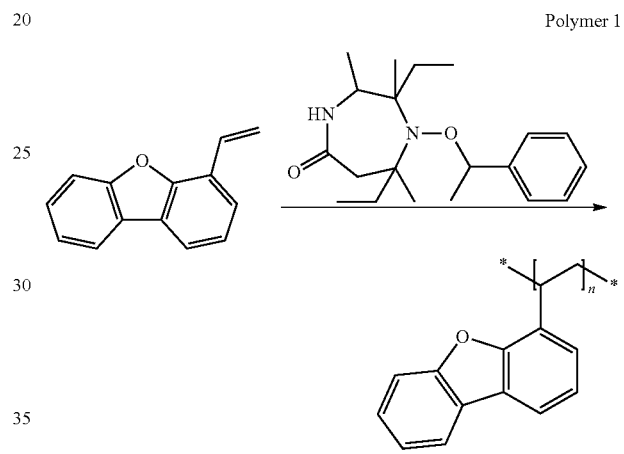

1 g 4-Vinyl-dibenzofuran (example 1) and 0.01 eq. of the initiator indicated in the above scheme are dissolved in 0.5 ml chlorobenzene, degassed and stirred under nitrogen at 120° C. for 24 h. The product is purified by multiple precipitation in MeOH. Yield 70%. GPC: Mn=13600, PDI=1.16.

Example 4

Polymer 2

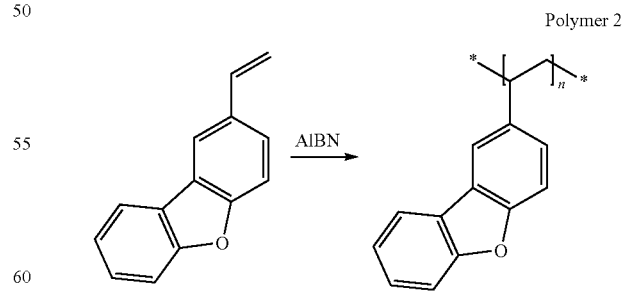

1.24 g 2-Vinyl-dibenzofurane (example 2) and 1.5 weight % of AIBN are dissolved in 5 ml toluene, degassed and polymerized under inert atmosphere for 24 h at 80° C. The polymer is purified by multiple precipitation in methanol. Yield 83%. GPC: Mn=19800, PDI=1.96.

Example 5

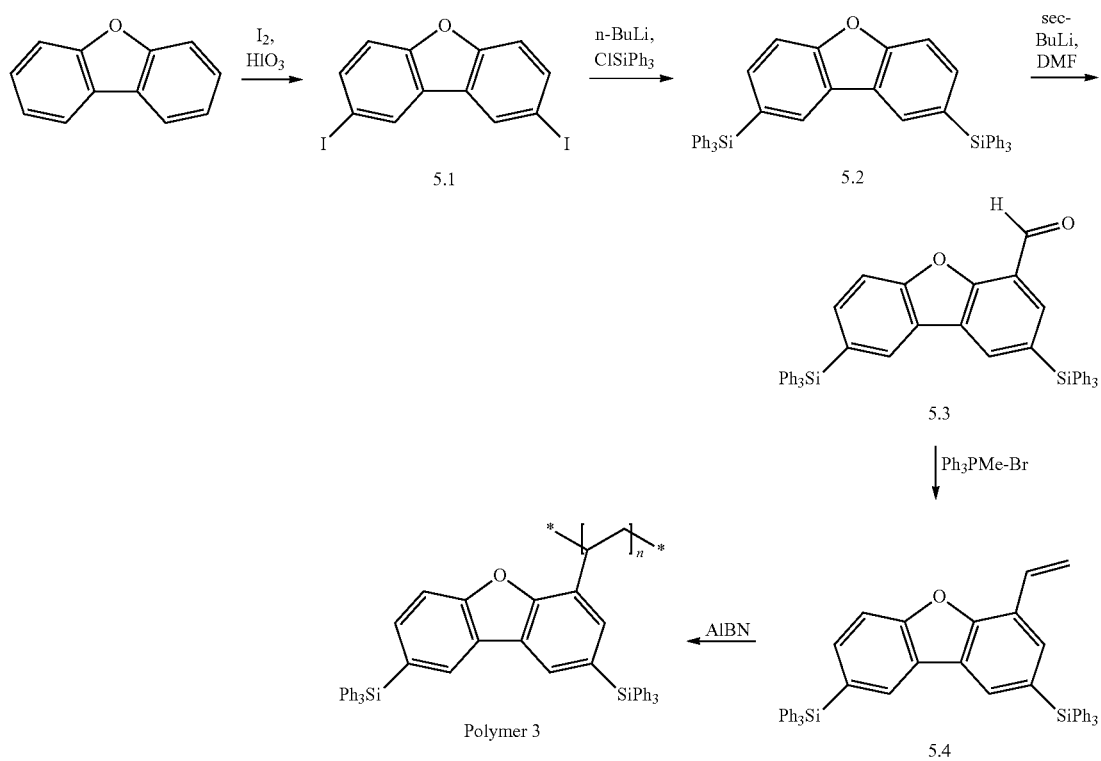

16.8 g (90.1 mmol) of benzofurane, 19.7 g (80 mmol) iodine, 7.7 g (44 mmol) Iodic acid are dissolved in 200 ml acidic acid, 15 ml water, 2 ml sulphuric acid and 10 ml carbon tetrachloride, and stirred at 65° C. for 30 h. The product is filtered off, redissolved in hot toluene and precipitated again by adding methanol. 2,8-Diiododibenzofurane (5.1) is isolated in 60.7% yield.

$^{1}$H-NMR (300 MHz, CDCl$_{3}$):
8.2 (s, 2H)
7.74 (d, 2H)
7.33 (d, 2H)

4 g (13.5 mmol) of 2,8-Diiododibenzofurane are dissolved in 100 ml of dry THF. 17.8 ml of 1,6M n-Buthyllithium solution in hexane is added dropwise at −78° C. After stirring for 1 h at −78° C., a solution of 8.8 g (29.84 mmol) of chlorotriphenylsilane in 20 ml THF is added. The reaction mixture is allowed to warm to RT and is quenched with saturated ammonium chloride solution. The organic phase is filtered and the product purified by recrystallization from THF, resulting in 5.62 g (60%) of 2,8-di-(triphenylsilyl)-dibenzofurane (5.2).

$^{1}$H-NMR (300 MHz, CDCl$_{3}$):
8.08 (s, 2H)
6.68-7.58 (m, 16H)
7.49-7.36 (m, 18H)

1 g (1.46 mmol) 2,8-di-(triphenylsilyl)-dibenzofuran are dissolved in 100 ml dry THF at 45° C. and 10 ml of 1.4 M sec-Buthyllithium solution in cyclohexane is added. After stirring for 15 min. at 45° C., 2 ml of dry DMF is added; the reaction mixture is stirred for 1 h. 100 ml of 0.5 M HCl is added to quench the reaction. The product is extracted with ethylacetate and purified by column chromatography on silica gel with heptane:ethylacetate (3:1) as an eluent. 2,8-di-(triphenylsilyl)-dibenzofuran-4-carboxaldehyde (5.3) is obtained in 30.2% yield.

$^{1}$H-NMR (300 MHz, CDCl$_{3}$):
10.5 (s, 1H)
8.30 (s, 1H)
8.15 (s, 1H)
8.11 (s, 1H)
7.73-7.55 (m, 14H)
7.49-7.36 (m, 18H)

2,8-Di-(triphenylsilyl)-dibenzofuran-4-carboxaldehyde is reacted with Methyl triphenylphosphonium bromide according to the method of example 2 to give 4-Vinyl-2.8-di-(triphenylsilyl)-dibenzofurane (5.4) in 37.8% yield.

$^{1}$H-NMR (300 MHz, CDCl$_{3}$):
7.99 (s, 1H)
7.88 (s, 1H)
7.57-7.48 (m, 15H)
7.40-7.26 (m, 18H)
6.93 (dd, 1H)
6.14 (d, 1H)
5.46 (d, 1H)

Polymer 3 is obtained according to the method of example 4 in 30% yield. GPC: Mn=6400, PDI=1.26.

Example 6
In analogy to the methods given in example 5 and according to the following reaction scheme, polymers 4 and 5 are obtained:
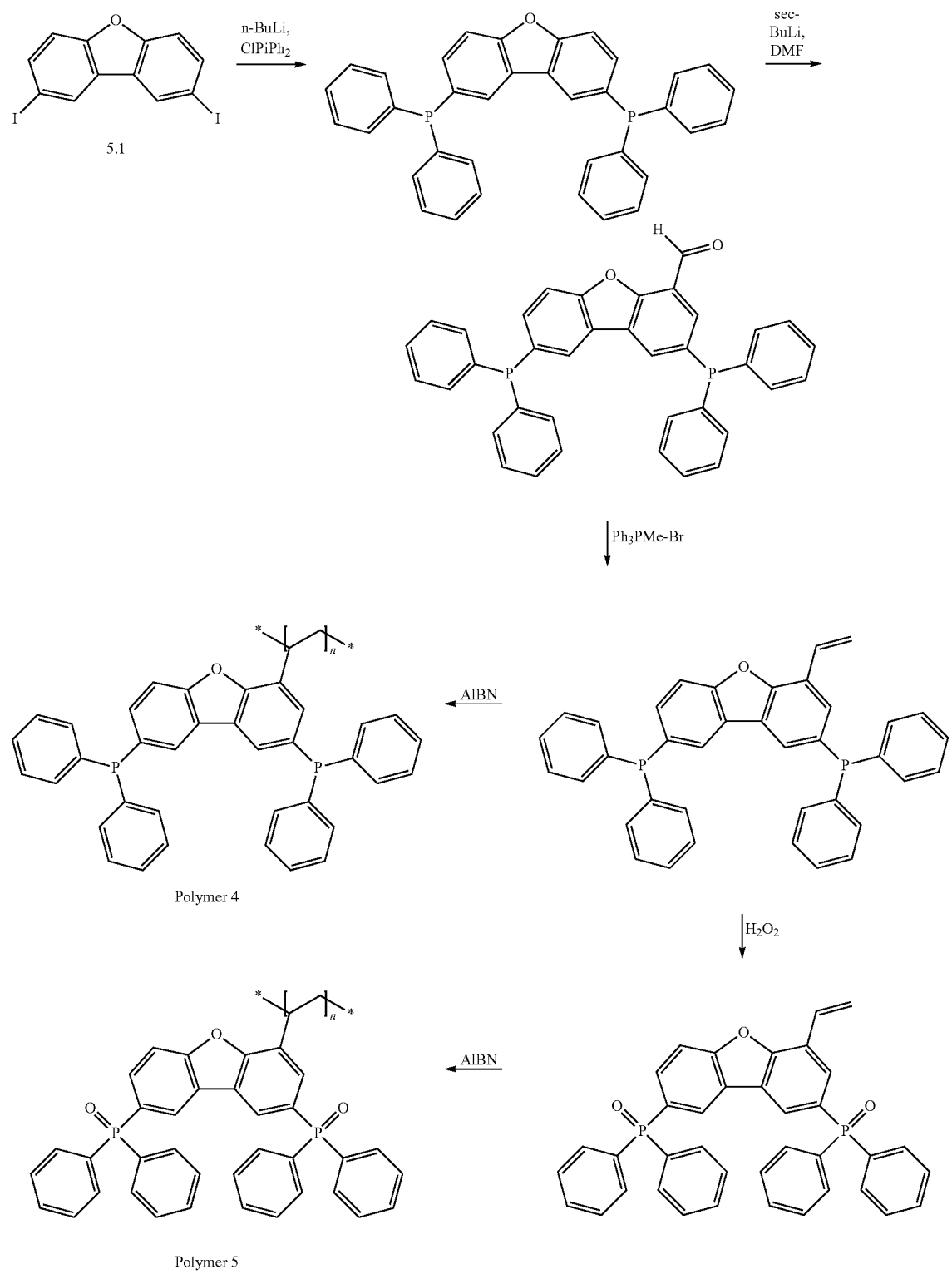

Example 7

In analogy to the methods given in example 5 and according to the following reaction scheme, polymer 6 is obtained:

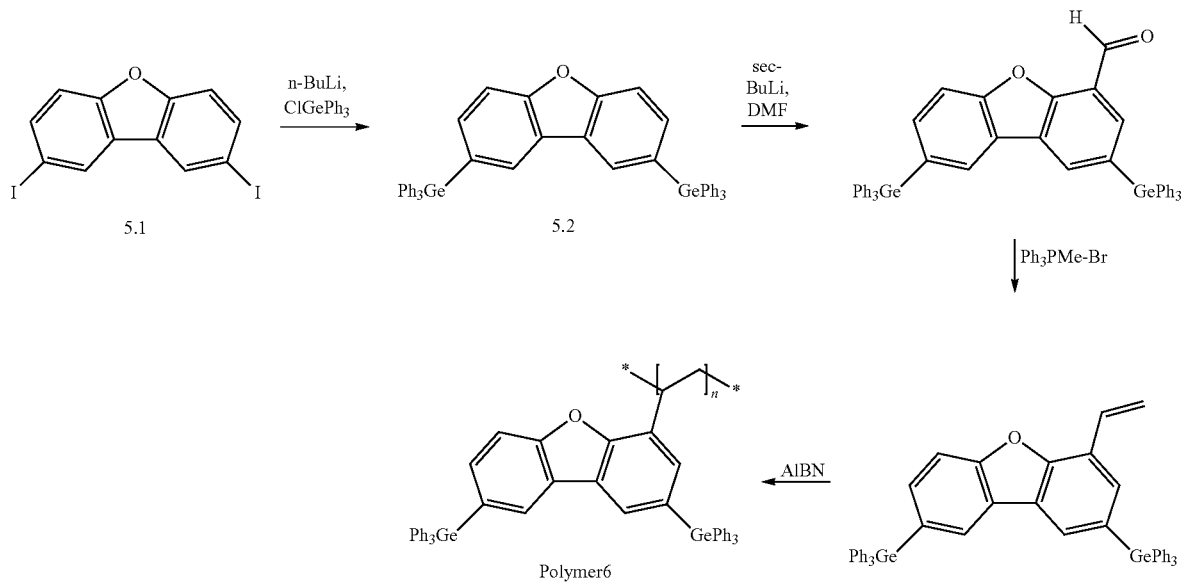

Application Examples

An organic luminescence device having a single organic layer is prepared in the following manner: On a glass substrate, a 80 nm thick ITO film is formed by sputtering and subsequently patterned. Onto the oxygen-plasma treated ITO film, a hole-injection layer of 80 nm thickness is formed by spin-coating using PEDOT:PSS (Baytron P), followed by heating at 200° C. (10 minutes). A solution of 15 mg of a polymer of the invention, 1.25 mg of TPD, 7.5 mg of PBD and 1.25 mg of Ir(ppy)$_3$ in 1.1 ml of toluene is applied by spin coating (3100 rpm.; 40 seconds) to obtain a thickness of 80 nm. The film is dried under nitrogen atmosphere at 80° C. for 30 minutes. The substrate is placed in a vacuum deposition chamber, and a cathode having a two-layer structure is formed by depositing a 5 nm layer of barium followed by a 70 nm layer of aluminum. Details of operating and device efficiency are compiled in the following table.

| Compound | Max. QE in % | cd/A @ 1000 cd/qm | V @ 1000 cd/qm | CIE x | CIE y |
|---|---|---|---|---|---|
| Polymer 1 | | 8.8 | 12.0 | 0.3 | 0.63 |
| Polymer 2 | 3.07 | 9.8 | 12.3 | 0..3 | 0.63 |

The invention claimed is:

1. Electroluminescent composition comprising a homopolymer of formula III

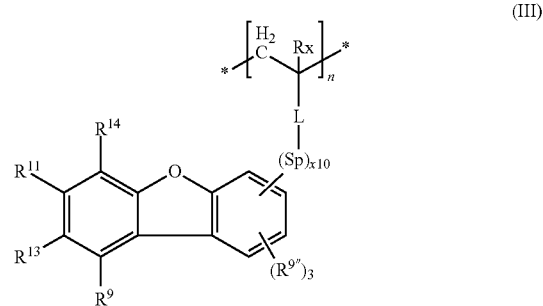

wherein n ranges from 2 to 10000;

L is $CH_2$, CO or a direct bond;

$R^9$, $R^{11}$, $R^{13}$, $R^{14}$, are selected from H, $C_1$-$C_{18}$alkyl, halogen, $C_1$-$C_{18}$alkyl which is substituted by E and/or interrupted by D, $C_6$-$C_{24}$aryl, $C_6$-$C_{24}$aryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, SiRR'R", GeRR'R", POAr$_2$, PAr$_2$, or is —CO—$R^{28}$;

each of the residues $R^{9'''}$ is independently selected from those defined for $R^9$, Rx is H or methyl, SP is a divalent organic spacer, X10 is o or 1;

D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; —CN; or halogen;

G is E, $C_1$-$C_{18}$alkyl, $C_3$-$C_{12}$cycloalkyl, $C_2$-$C_{18}$alkyl which is interrupted by D, $C_1$-$C_{18}$perfluoroalkyl, or $C_1$-$C_{18}$alkoxy which is substituted by E and/or interrupted by D, wherein $R^{23}$, $R^{24}$, $R^{25}$ and $R^{26}$ are independently of each other H; $C_6$-$C_{18}$aryl; $C_6$-$C_{18}$arylalkyl; $C_3$-$C_{12}$cycloalkyl; $C_6$-$C_{18}$aryl or $C_6$-$C_{18}$arylalkyl which is substituted by $C_1$-$C_{18}$alkyl and/or $C_1$-$C_{18}$alkoxy; $C_1$-$C_{18}$alkyl; or $C_2$-$C_8$alkyl which is interrupted by —O—; or $R^{25}$ and $R^{26}$ together form a five or six membered ring;

$R^{27}$ and $R^{28}$ are independently of each other H; $C_6$-$C_{18}$aryl; $C_6$-$C_{18}$arylalkyl; $C_6$-$C_{18}$aryl or $C_6$-$C_{18}$arylalkyl which is substituted by $C_1$-$C_{18}$alkyl and/or $C_1$-$C_{18}$alkoxy; $C_1$-$C_{18}$alkyl; $C_3$-$C_{12}$cycloalkyl; or $C_2$-$C_{18}$alkyl which is interrupted by —O—;

$R^{29}$ is H; $C_6$-$C_{18}$aryl; $C_6$-$C_{18}$arylalkyl; $C_6$-$C_{18}$aryl or $C_6$-$C_{18}$arylalkyl which is substituted by $C_1$-$C_{18}$alkyl and/or $C_1$-$C_{18}$alkoxy; $C_1$-$C_{18}$alkyl; $C_2$-$C_{18}$alkylcarbonyl; $C_3$-$C_{12}$cycloalkyl; or $C_2$-$C_{18}$alkyl or $C_2$-$C_8$alkylcarbonyl which is interrupted by —O—;

$R^{30}$ and $R^{31}$ are independently of each other $C_1$-$C_{18}$alkyl, $C_3$-$C_{12}$cycloalkyl, $C_6$-$C_{18}$aryl, or $C_6$-$C_{18}$aryl, which is substituted by $C_1$-$C_{18}$alkyl, and $R^{32}$ is $C_1$-$C_{18}$alkyl, $C_6$-$C_{18}$aryl, or $C_6$-$C_{18}$aryl, which is substituted by $C_1$-$C_{18}$alkyl, R, R' and R" independently are selected from $C_1$-$C_{12}$alkyl, $C_1$-$C_{12}$haloalkyl, $C_5$-$C_{10}$aryl, $C_3$-$C_{12}$cycloalkyl; and Ar independently is selected from $C_5$-$C_{10}$aryl, or $C_5$-$C_{10}$aryl which is substituted by $C_1$-$C_{18}$alkyl; and a luminescent component selected from phosphorescent metal complexes and fluorescent dopants.

2. Electroluminescent composition of claim 1, wherein n ranges from 5 to 5000;

X10 is 0;

$R^9$, $R^{9'''}$, $R^{11}$, $R^{13}$, $R^{14}$, are selected from H, $C_1$-$C_8$alkyl, fluoro, $C_1$-$C_8$alkyl which is substituted by E, $C_2$-$C_{18}$alkyl which is interrupted by D, phenyl, phenyl which is substituted by G, $C_2$-$C_8$alkenyl, $C_2$-$C_8$alkynyl, $C_1$-$C_8$alkoxy, $C_1$-$C_8$alkoxy which is substituted by E, $C_2$-$C_{18}$alkoxy which is interrupted by D, $C_7$-$C_{25}$phenylalkyl, SiRR'R", GeRR'R", POAr$_2$, PAr$_2$, or is —CO—$R^{28}$;

D is —CO—; —COO—; —S—; —SO—; —SO$_2$—; —O—; —NR$^{25}$—; —SiR$^3$OR$^{31}$—; —POR$^{32}$—; and E is —OR$^{29}$; —NR$^{25}$R$^{26}$; —COR$^{28}$; —COOR$^{27}$; —CONR$^{25}$R$^{26}$; —CN; or halogen;

G is E, $C_1$-$C_8$alkyl, cyclohexyl, $C_2$-$C_{18}$alkyl which is interrupted by D, $C_1$-$C_8$ perfluoroalkyl, $C_1$-$C_{18}$alkoxy which is substituted by E, $C_2$-$C_{18}$alkoxy which is interrupted by D, wherein $R^{25}$ and $R^{26}$ are independently of each other H; phenyl; $C_7$-$C_{12}$phenylalkyl; cyclohexyl; phenyl or $C_7$-$C_{12}$phenylalkyl which is substituted by $C_1$-$C_8$alkyl or $C_1$-$C_8$alkoxy; $C_1$-$C_{18}$alkyl; or $C_2$-$C_{18}$alkyl which is interrupted by —O—; or $R^{25}$ and $R^{26}$ together form a five or six membered ring selected from

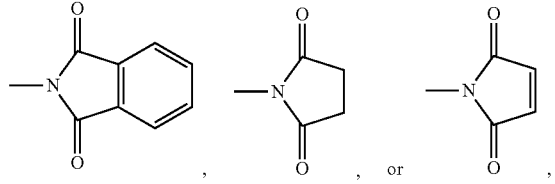

$R^{27}$ and $R^{28}$ are independently of each other H; phenyl; $C_7$-$C_{12}$phenylalkyl; phenyl or $C_7$-$C_{12}$phenylalkyl which is substituted by $C_1$-$C_8$alkyl and/or $C_1$-$C_8$alkoxy; $C_1$-$C_8$alkyl; cyclohexyl; or $C_2$-$C_{18}$alkyl which is interrupted by —O—;

$R^{29}$ is H; phenyl; $C_7$-$C_{12}$phenylalkyl; phenyl or $C_7$-$C_{12}$phenylalkyl which is substituted by $C_1$-$C_8$alkyl and/or $C_1$-$C_8$alkoxy; $C_1$-$C_8$alkyl; $C_2$-$C_8$alkylcarbonyl; cyclohexyl; or $C_2$-$C_{18}$alkyl or $C_2$-$C_{18}$alkylcarbonyl which is interrupted by —O—;

$R^{30}$ and $R^{31}$ are independently of each other $C_1$-$C_8$alkyl, phenyl, or phenyl which is substituted by $C_1$-$C_8$alkyl, and $R^{32}$ is $C_1$-$C_8$alkyl, phenyl, or phenyl which is substituted by $C_1$-$C_8$alkyl, R, R' and R" independently are selected from $C_1$-$C_6$alkyl, phenyl, cyclopentyl, cyclohexyl; and Ar is phenyl or phenyl substituted by $C_1$-$C_8$alkyl.

3. Electroluminescent composition according to claim 1 containing 10 to 1000 structural units of the formula, wherein X10 is 0;

any of $R^9$, $R^{9'''}$, $R^{11}$, $R^{13}$, $R^{14}$, independently is selected from H, $C_1$-$C_8$alkyl, fluoro, $C_1$-$C_8$alkyl which is substituted by E, $C_2$-$C_{18}$alkyl which is interrupted by D, phenyl, phenyl which is substituted by G, $C_2$-$C_8$alkenyl, $C_2$-$C_8$alkynyl, $C_1$-$C_8$alkoxy, $C_1$-$C_8$alkoxy which is substituted by E, $C_2$-$C_{18}$alkoxy which is interrupted by D, $C_7$-$C_{25}$phenylalkyl, SiRR'R", GeRR'R", POAr$_2$, PAr$_2$, or is —CO—$R^{28}$;

D is —CO—; —COO—; —O—; —NR$^{25}$—; —SiR$^3$OR$^{31}$—; and

E is -OR$^{29}$; —NR$^{25}$R$^{26}$; —COR$^{28}$; —COOR$^{27}$; —CONR$^{25}$R$^{26}$; or fluoro;

G is E or $C_1$-$C_8$alkyl;

$R^{25}$ and $R^{26}$ are independently of each other H; $C_1$-$C_8$alkyl; cyclohexyl;

$R^{27}$ and $R^{28}$ are independently of each other H; phenyl; benzyl; phenyl or benzyl which is substituted by $C_1$-$C_8$alkyl and/or $C_1$-$C_8$alkoxy; $C_1$-$C_8$alkyl;

$R^{29}$ is H; phenyl; benzyl; phenyl or benzyl which is substituted by $C_1$-$C_8$alkyl and/or $C_1$-$C_8$alkoxy; $C_1$-$C_8$alkyl; acetyl; cyclohexyl; or $C_2$-$C_{12}$alkyl which is interrupted by —O—;

$R^{30}$ and $R^{31}$ are independently of each other methyl or phenyl, and

R, R' and R" independently are selected from methyl, ethyl, phenyl; and

Ar is phenyl.

4. Electroluminescent composition of claim 1, wherein any of $R^9$, $R^{9'''}$, $R^{11}$, $R^{13}$, $R^{14}$, independently is selected from H, $C_1$-$C_8$alkyl, SiRR'R".

5. Electroluminescent composition as defined in claim 1, which comprises one or more further component(s) selected from electron transporters, hole transporters, inert polymers, viscosity modifiers, initiators, organic salts, and stabilizers.

6. An organic electronic device, comprising a layer of an electroluminescent material according to claim 1.

7. A device according to claim 6 selected from stationary and mobile displays.

8. Homopolymer of the formula III'

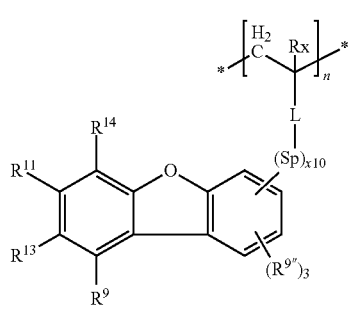

wherein
n ranges from 5 to 10000;
at least one of the residues $R^9$, $R^{9'''}$, $R^{11}$, $R^{13}$, $R^{14}$ is selected from $C_1$-$C_{18}$alkyl, halogen, $C_1$-$C_{18}$alkyl which is substituted by E and/or interrupted by D, $C_6$-$C_{24}$aryl, $C_6$-$C_{24}$aryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, SiRR'R", GeRR'R", POAr$_2$, PAr$_2$, CO—$R^{28}$;
while the remaining residues may also be hydrogen;
D is —CO—; —COO—; —S—; —SO—; —SO$_2$—; —O—; —NR$^{25}$—; —SiR$^3$OR$^{31}$—; —POR$^{32}$—; and
E is —OR$^{29}$; —NR$^{25}$R$^{26}$; —COR$^{28}$; —COOR$^{27}$; —CONR$^{25}$R$^{26}$; —CN; or halogen;
G is E, $C_1$-$C_8$alkyl, cyclohexyl, $C_2$-$C_{18}$alkyl which is interrupted by D, $C_1$-$C_8$ perfluoroalkyl, $C_2$-$C_{18}$alkoxy which is substituted by E, $C_2$-$C_{18}$alkoxy which is interrupted by D, wherein
$R^{25}$ and $R^{26}$ are independently of each other H; phenyl; $C_7$-$C_{12}$phenylalkyl; cyclohexyl; phenyl or $C_7$-$C_{12}$phenylalkyl which is substituted by $C_1$-$C_8$alkyl or $C_1$-$C_8$alkoxy; $C_1$-$C_8$alkyl; or $C_2$-$C_{18}$alkyl which is interrupted by —O—; or
$R^{25}$ and $R^{26}$ together form a five or six membered ring selected from

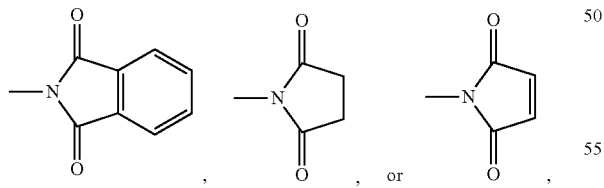

$R^{27}$ and $R^{28}$ are independently of each other H; phenyl; $C_7$-$C_{12}$phenylalkyl; phenyl or $C_7$-$C_{12}$phenylalkyl which is substituted by $C_1$-$C_8$alkyl and/or $C_1$-$C_8$alkoxy; $C_1$-$C_8$alkyl; cyclohexyl; or $C_2$-$C_{18}$alkyl which is interrupted by —O—;

$R^{29}$ is H; phenyl; $C_7$-$C_{12}$phenylalkyl; phenyl or $C_7$-$C_{12}$phenylalkyl which is substituted by $C_1$-$C_8$alkyl and/or $C_1$-$C_8$alkoxy; $C_1$-$C_8$alkyl; $C_2$-$C_8$alkylcarbonyl; cyclohexyl; or $C_2$-$C_{18}$alkyl or $C_2$-$C_{18}$alkylcarbonyl which is interrupted by —O—;

$R^{39}$ and $R^{31}$ are independently of each other $C_1$-$C_8$alkyl, phenyl, or phenyl which is substituted by $C_1$-$C_8$alkyl, and $R^{32}$ is $C_1$-$C_8$alkyl, phenyl, or phenyl which is substituted by $C_1$-$C_8$alkyl, R, R' and R" independently are selected from $C_1$-$C_6$alkyl, phenyl, cyclopentyl, cyclohexyl; and Ar is phenyl or phenyl substituted by $C_1$-$C_8$alkyl;

L is CH$_2$, CO or a direct bond; Rx is H or methyl;

X10 is 0 or 1 and Sp is O, $C_1$-$C_4$alkylene-O, CH$_2$—CHOH—CH$_2$—O, COO, CONR22, $C_1$-$C_4$alkylene, or CH$_2$CHOHCH$_2$.

9. Compound of the formula V

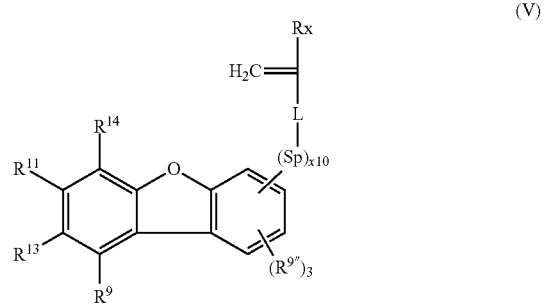

wherein
at least one of the residues $R^9$, $R^{9'''}$, $R^{11}$, $R^{13}$, $R^{14}$ is selected from halogen, $C_2$-$C_{18}$alkynyl, $C_1$-$C_{18}$alkoxy, SiRR'R", GeRR'R", POAr$_2$, PAr$_2$;

R, R' and R" independently are selected from $C_1$-$C_6$alkyl, phenyl, cyclopentyl, cyclohexyl; and Ar is phenyl or phenyl substituted by $C_1$-$C_8$alkyl;

L is CH$_2$, CO or a direct bond; Rx is H or methyl;

X10 is 0 or 1 and Sp is O, $C_1$-$C_4$alkylene-O, CH$_2$—CHOH—CH$_2$—O, COO, CONR22, $C_1$-$C_4$alkylene, or CH$_2$CHOHCH$_2$.

* * * * *